(12) United States Patent
Lee et al.

(10) Patent No.: US 9,343,494 B2
(45) Date of Patent: May 17, 2016

(54) LIGHT GUIDED PIXEL CONFIGURED FOR EMISSIONS DETECTION AND COMPRISING A GUIDE LAYER WITH A WAVELENGTH SELECTIVE FILTER MATERIAL AND A LIGHT DETECTOR LAYER

(75) Inventors: Seung Ah Lee, Pasadena, CA (US); Guoan Zheng, Pasadena, CA (US); Benjamin Judkewitz, Los Angeles, CA (US); Shuo Pang, Pasadena, CA (US); Jigang Wu, Shanghai (CN); Changhuei Yang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 239 days.

(21) Appl. No.: 13/411,103

(22) Filed: Mar. 2, 2012

(65) Prior Publication Data

US 2012/0223214 A1    Sep. 6, 2012

Related U.S. Application Data

(60) Provisional application No. 61/448,964, filed on Mar. 3, 2011.

(51) Int. Cl.
*H01L 27/146* (2006.01)

(52) U.S. Cl.
CPC .... *H01L 27/14629* (2013.01); *H01L 27/14621* (2013.01)

(58) Field of Classification Search
CPC .................. H01L 27/14629; H01L 27/14621

USPC .............. 250/227.11, 216, 559.4, 221, 208.1, 250/363.01–363.03, 366–368, 370.11, 362; 385/12, 14, 31, 33, 141, 143; 356/36, 356/318, 319, 369
See application file for complete search history.

(56) References Cited

U.S. PATENT DOCUMENTS

| 3,736,432 | A |   | 5/1973  | Sweet            |         |
|-----------|---|---|---------|------------------|---------|
| 5,225,057 | A |   | 7/1993  | LeFebvre et al.  |         |
| 5,349,191 | A | * | 9/1994  | Rogers           | 250/367 |
| 5,420,959 | A | * | 5/1995  | Walker et al.    | 385/143 |
| 5,495,337 | A |   | 2/1996  | Goshorn et al.   |         |
| 5,545,561 | A |   | 8/1996  | Lleonart Aliberas|         |
| 5,684,906 | A | * | 11/1997 | Sugawara         | 385/120 |

(Continued)

FOREIGN PATENT DOCUMENTS

CN    101655463 A    2/2010
DE    202 14 835 U1  1/2003

(Continued)

OTHER PUBLICATIONS

United States Patent and Trademark Office (USPTO) Non-Final Office Action in U.S. Appl. No. 13/069,651 dated on Mar. 28, 2014.

(Continued)

*Primary Examiner* — Que T Le
(74) *Attorney, Agent, or Firm* — Sheila Martinez-Lemke; Weaver Austin Villeneuve & Sampson LLP

(57) ABSTRACT

A light guided pixel having a guide layer and a light detector layer. The guide layer has a light guide. The light detector layer has a light detecting element that receives light channeled by the light guide. The light guide may include a filter for channeling emissions to the light detecting element.

21 Claims, 9 Drawing Sheets

(56) References Cited

U.S. PATENT DOCUMENTS

| | | |
|---|---|---|
| 5,796,112 A | 8/1998 | Ichie |
| 5,892,577 A | 4/1999 | Gordon |
| 6,058,209 A | 5/2000 | Vaidyanathan et al. |
| 6,147,798 A | 11/2000 | Brooker et al. |
| 6,194,718 B1 | 2/2001 | Dotan |
| 6,215,114 B1 | 4/2001 | Yagi et al. |
| 6,519,313 B2 * | 2/2003 | Venkataramani et al. ...... 378/19 |
| 6,555,816 B1 | 4/2003 | Sawahata et al. |
| 6,608,717 B1 | 8/2003 | Medford et al. |
| 6,784,417 B2 * | 8/2004 | Sonoki ............... 250/231.13 |
| 6,903,820 B2 | 6/2005 | Wang |
| 6,937,323 B2 | 8/2005 | Worthington et al. |
| 6,944,322 B2 | 9/2005 | Johnson et al. |
| 7,142,296 B2 | 11/2006 | Cunningham et al. |
| 7,250,598 B2 | 7/2007 | Hollingsworth et al. |
| 7,253,947 B2 | 8/2007 | Bromage et al. |
| 7,369,234 B2 | 5/2008 | Beaglehole |
| 7,418,118 B2 | 8/2008 | Furnas et al. |
| 7,705,331 B1 | 4/2010 | Kirk et al. |
| 7,892,168 B2 | 2/2011 | Sano |
| 7,986,824 B2 | 7/2011 | Suzuki et al. |
| 8,139,106 B2 | 3/2012 | Maiya |
| 8,345,351 B2 | 1/2013 | Takeuchi |
| 8,498,681 B2 | 7/2013 | Wang et al. |
| 8,526,006 B2 | 9/2013 | Nebosis et al. |
| 8,730,574 B2 | 5/2014 | Araya et al. |
| 8,837,045 B2 | 9/2014 | Popescu et al. |
| 8,855,265 B2 | 10/2014 | Engel et al. |
| 8,928,890 B2 | 1/2015 | Nebosis et al. |
| 8,946,619 B2 | 2/2015 | Wu et al. |
| 8,964,017 B2 | 2/2015 | Vertikov et al. |
| 8,970,671 B2 | 3/2015 | Parvani et al. |
| 2002/0070350 A1 | 6/2002 | Rushbrooke et al. |
| 2002/0080240 A1 | 6/2002 | Omi |
| 2003/0012277 A1 | 1/2003 | Azuma et al. |
| 2003/0032039 A1 | 2/2003 | Cunningham et al. |
| 2004/0135079 A1 | 7/2004 | Moellmann |
| 2004/0146965 A1 | 7/2004 | Brayton |
| 2004/0264637 A1 | 12/2004 | Wang |
| 2005/0013478 A1 | 1/2005 | Oba et al. |
| 2005/0078362 A1 | 4/2005 | Borlinghaus |
| 2006/0007436 A1 | 1/2006 | Kurosawa et al. |
| 2006/0077535 A1 | 4/2006 | Luther et al. |
| 2006/0092503 A1 | 5/2006 | Saunders |
| 2006/0124870 A1 | 6/2006 | Bobanovic et al. |
| 2006/0227328 A1 | 10/2006 | Vanwiggeren et al. |
| 2007/0046924 A1 | 3/2007 | Chang |
| 2007/0052953 A1 | 3/2007 | Hill |
| 2007/0058054 A1 | 3/2007 | Kagayama et al. |
| 2007/0081200 A1 | 4/2007 | Zomet et al. |
| 2007/0207061 A1 | 9/2007 | Yang et al. |
| 2007/0229852 A1 | 10/2007 | Wack et al. |
| 2007/0236782 A1 | 10/2007 | Sano |
| 2008/0056610 A1 | 3/2008 | Kanda |
| 2008/0144029 A1 | 6/2008 | Li |
| 2008/0158566 A1 | 7/2008 | Suzuki et al. |
| 2008/0174862 A1 | 7/2008 | Focht |
| 2008/0204551 A1 | 8/2008 | O'Connell et al. |
| 2008/0213141 A1 | 9/2008 | Pinchot |
| 2008/0214412 A1 | 9/2008 | Stahler et al. |
| 2008/0259345 A1 | 10/2008 | Fukutake |
| 2009/0086314 A1 | 4/2009 | Namba et al. |
| 2009/0091811 A1 | 4/2009 | Asundi et al. |
| 2009/0122070 A1 | 5/2009 | Aragaki et al. |
| 2009/0166518 A1 | 7/2009 | Tay et al. |
| 2009/0180179 A1 | 7/2009 | Ryu |
| 2009/0225309 A1 | 9/2009 | Demou |
| 2009/0225319 A1 | 9/2009 | Lee et al. |
| 2009/0237502 A1 | 9/2009 | Maiya |
| 2009/0268280 A1 | 10/2009 | Osawa et al. |
| 2009/0273829 A1 | 11/2009 | Terakawa et al. |
| 2009/0276188 A1 | 11/2009 | Cui et al. |
| 2010/0033561 A1 | 2/2010 | Hersee |
| 2010/0045955 A1 | 2/2010 | Vladimirsky et al. |
| 2010/0108873 A1 | 5/2010 | Schwertner |
| 2010/0308427 A1 | 12/2010 | Lenchenkov |
| 2011/0001815 A1 | 1/2011 | Nakano et al. |
| 2011/0063592 A1 | 3/2011 | Ezura et al. |
| 2011/0069382 A1 | 3/2011 | Toomre et al. |
| 2011/0098950 A1 | 4/2011 | Carr |
| 2011/0102888 A1 | 5/2011 | Honda et al. |
| 2011/0234757 A1 | 9/2011 | Zheng et al. |
| 2011/0266181 A1 | 11/2011 | Morozov |
| 2012/0086995 A1 | 4/2012 | Gerchberg et al. |
| 2012/0098950 A1 | 4/2012 | Zheng et al. |
| 2012/0099803 A1 | 4/2012 | Ozcan et al. |
| 2012/0157160 A1 | 6/2012 | Ozcan et al. |
| 2012/0218379 A1 | 8/2012 | Ozcan et al. |
| 2012/0223217 A1 | 9/2012 | Zheng et al. |
| 2012/0228475 A1 | 9/2012 | Pang et al. |
| 2012/0248292 A1 | 10/2012 | Ozcan et al. |
| 2012/0258525 A1 | 10/2012 | Iizumi et al. |
| 2012/0275681 A1 | 11/2012 | Honda et al. |
| 2014/0133702 A1 | 5/2014 | Zheng et al. |

FOREIGN PATENT DOCUMENTS

| | | |
|---|---|---|
| EP | 1 956 360 | 8/2008 |
| FR | 2 602 241 | 2/1988 |
| JP | 2010-020151 A | 1/2010 |
| JP | 2013-542468 A | 11/2013 |
| JP | 2014-515179 A | 6/2014 |
| WO | WO 91/09300 | 6/1991 |
| WO | WO 2009/113544 | 9/2009 |
| WO | WO 2011/119678 | 9/2011 |
| WO | WO 2011/139641 | 11/2011 |
| WO | WO 2012/058233 | 5/2012 |
| WO | WO 2012/094523 | 7/2012 |
| WO | WO 2012/119094 | 9/2012 |
| WO | WO 2012/119114 | 9/2012 |

OTHER PUBLICATIONS

United States Patent and Trademark Office (USPTO) Non-Final Office Action in U.S. Appl. No. 13/281,287 dated on Oct. 31, 2013.

United States Patent and Trademark Office (USPTO) Final Office Action in U.S. Appl. No. 13/281,287 dated on Mar. 12, 2014.

PCT International Search Report dated Dec. 7, 2011 issued in PCT/US2011/029542.

PCT International Preliminary Report on Patentability and Written Opinion dated Oct. 4, 2012 issued in PCT/US2011/029542.

Chinese First Office Action dated Jan. 23, 2014 issued in CN 201180012251.6.

European Search Report dated Jun. 25, 2014 issued in EP 11 760 112.0.

PCT International Search Report dated May 8, 2012 issued in PCT/US2011/057735.

PCT International Preliminary Report on Patentability and Written Opinion dated May 10, 2013 issued in PCT/US2011/057735.

European Search Report dated Jun. 25, 2014 issued in EP 11 836 959.

European Office Action dated Jul. 3, 2014 issued in EP 11 836 959.4.

PCT International Search Report and Written Opinion dated Sep. 25, 2012 issued in PCT/US2012/027575.

PCT International Preliminary Report on Patentability and Written Opinion dated Sep. 12, 2013 issued in PCT/US2012/027575.

European Search Report dated Jun. 25, 2014 issued in EP 12 75 2493.

PCT International Search Report and Written Opinion dated Sep. 21, 2012 issued in PCT/US2012/027522.

PCT International Preliminary Report on Patentability and Written Opinion dated Sep. 12, 2013 issued in PCT/US2012/027522.

European Supplementary Search Report dated Jun. 25, 2014 issued in EP 12 75 2808.

Bishara et al., (May 24, 2010) "Lensfree on-chip microscopy over a wide field-of-view using pixel super-resolution," opticsinfobase.org, *Opt. Expr.* 18(11):11181-11191.

Cui, Xiquan, et al., (Aug. 5, 2008) "Lensless high-resolution on-chip optofluidic microscopes for *Caenorhabditis elegans* and cell imaging," *Proceedings of the National Academy of Sciences of the United States of America*, 105(31):10670-10675.

(56) References Cited

OTHER PUBLICATIONS

Elad, M., and Hel-Or, Y., (Dec. 1998) "A Fast Super-Resolution Reconstruction Algorithm for Pure Translational Motion and Common Space-Invariant Blur," *IEEE Transactions on Image Processing*, 10:1187-1193.
Farsiu, S. et al., (Jan. 2004) "Advances and challenges in super-resolution," *Wiley Periodicals*, 14:47-57.
Farsiu, S., et al., (Oct. 2004) "Fast and robust multiframe super resolution," *IEEE Transactions on Image Processing*, 13(10):1327-1344.
Gillette, J., et al., (1995) "Aliasing reduction in staring infrared imagers utilizing subpixel techniques," *Optical Engineering*, 34:3130.
Hardie Russell C., et al., (Apr. 1997) "High resolution image reconstruction from a sequence of rotated and translated frames and its application to an infrared imaging system," *Optical Engineering*, 27 pp.
Heng, Xin, et al., (2006) "Characterization of light collection through a subwavelength aperture from a point source," *Optics Express*, 14:10410-10425.
Heng, Xin, et al., (Jul. 17, 2006) "Optofluidic Microscopy: A Novel High Resolution Microscope-on-a-Chip," *Leos Summer Topical Meetings, 2006 Digest of the Quebec City, QC, Canada* Jul. 17-19, 2006, Piscataway, NJ, USA, IEEE, 6(10):15-16.
Kapur, J., et al., (1985) "A New Method for Gray-Level Picture Thresholding Using the Entropy of the Histogram," *Computer vision, graphics, and image processing*, 29:273-285.
Lee, Seung Ah, et al., (Oct. 2011) "Color Capable Sub-Pixel Resolving Optofluidic Microscope and Its Application to Blood Cell Imaging for Malaria Diagnosis," *PLoS One* 6(10):e26127, 6 pages.
Lee, Seung, Ah, et al., (Mar. 20, 2012) "On-chip continuous monitoring of motile microorganisms on an ePetri platform," *Lab on a Chip* 12(13):2385-2390.
Liang, J. Z., et al., (Nov. 1997) "Supernormal vision and high-resolution retinal imaging through adaptive optics," *Journal of the Optical Society of America*, 14(11):2884-2892.
Lin, Z., and Shum, H.-Y., (2004) "Fundamental limits of reconstruction-based superresolution algorithms under local translation," *IEEE Transactions on Pattern Analysis and Machine Intelligence*, pp. 83-97.
Miao, Qin, et al., (2009) "Dual Modal three-dimensional Imaging of Single Cells using Optical Projection Tomography Microscope," *Journal of Biomedical Optics*, 14:3 pages.
Moon, SanJun, et al., (Jul. 15, 2009) "Integrating Microfluidics and Lensless Imaging for point-of-care testing," *Biosensors and Bioelectronics*, 24(11):3208-3214.
Park, Sung Cheol, et al., (2003) "Super-resolution image reconstruction: a technical overview," *IEEE Signal Processing Magazine*, pp. 21-36.
Pastrana, Erika (Dec. 2011) *Nature Methods*, 8(12):999, 1 page [doi:10.1038/nmeth.1786].
Psaltis, Demetri, et al., (Jul. 2006) "Developing optofluidic technology through the fusion of microfluidics and optics," *Nature*, 442:381-386.
Schultz, R., et al., (1998) "Subpixel Motion Estimation for Super-Resolution Image Sequence Enhancement," *Journal of Visual Communication and Image Representation*, 9(1):38-50.
Shi, J., et al., (2006) "Small-kernel superresolution methods for microscanning imaging systems," *Applied Optics*, 45(6):1203-1214.
Su, Ting-Wei, et al., (Apr. 26, 2010) "Multi-angle lensless digital holography for depth resolved imaging on a chip," *Optics Express*, OSA, Washington DC, US 18(9):1094-4087, 22pp.
Wang et al., (2009) "Characterization of acceptance angles of small circular apertures," *Optics Express* 17(26):23903-23913.
Wu, J., et al., (Jul. 1, 2010) "Wide field-of-view microscope based on holographic focus grid illumination," *Optics Letters*, 35(13):2188-2190.
Zheng, et al., (2010) "Sub-pixel resolving optofluidic microscope for on-chip cell imaging," *Lab on a Chip*, 10(2):3125-3129.
Zheng, et al., (2009) "Supplementary Information for: Sub-pixel resolving optofluidic microscope for on-chip cell imaging," *Supplementary Material (ESI) for Lap on a Chip*, 10:3 pages.
Zheng, et al., (Oct. 15, 2011) "Microscopy refocusing and dark-field imaging by using a simple LED array," *Optics Letters* 36(20):3987-3989.
Zheng et al., (2011) "The ePetri dish, an on-chip cell imaging platform based on subpixel perspective sweeping microscopy (SPSM)," 6 pages and "Supporting Information" 3 pages; *Proceedings of the National Academy of Science* 108(41):16889-94.
Zheng et al., (Jul. 28, 2013) "Wide-field, high-resolution Fourier ptychographic microscopy," *Nature Photonics | Advance Online Publication*, DOI: 10.1038/NPHOTON.2013.187, 19 pages.
United States Patent and Trademark Office (USPTO) Final Office Action in U.S. Appl. No. 13/069,651 dated on Nov. 25, 2014.
United States Patent and Trademark Office (USPTO) Office Action in U.S. Appl. No. 13/281,287 dated on Nov. 6, 2014.
United States Patent and Trademark Office (USPTO) Office Action in U.S. Appl. No. 13/411,302 dated on Jan. 5, 2015.
United States Patent and Trademark Office (USPTO) Office Action in U.S. Appl. No. 14/072,652 dated on Mar. 23, 2015.
Chinese Second Office Action dated Oct. 8, 2014 issued in CN 201180012251.6.
Chinese First Office Action [no translation] dated Jan. 20, 2015 issued in CN 201180048639.1.
Japanese Office Action [with translation] dated Oct. 28, 2014 issued in JP 2013536747.
Chinese First Office Action dated Feb. 28, 2015 issued in CN201280003668.
Tai, Y. C., et al., (2002) "Integrated micro/nano fluidics for mass-spectrometry protein analysis," *International Journal of Nonlinear Sciences and Numerical Simulation*, 3(3-4):739-741.
Yanowitz, et al., (2005) "Cyclin D involvement demarcates a late transition in *C. elegans* embryogenesis," *Developmental Biology*, 279:244-251.
United States Patent and Trademark Office (USPTO) Non-Final Office Action in U.S. Appl. No. 13/069,651 dated on Jul. 15, 2015.
United States Patent and Trademark Office (USPTO) Final Office Action in U.S. Appl. No. 13/281,287 dated on Jul. 1, 2015.
United States Patent and Trademark Office (USPTO) Final Office Action in U.S. Appl. No. 13/411,302 dated on Sep. 25, 2015.
United States Patent and Trademark Office (USPTO) Final Office Action in U.S. Appl. No. 14/072,652 dated on Nov. 6, 2015.
Chinese Third Office Action dated Apr. 27, 2015 issued in CN 201180012251.6.
European Examination Report dated Jun. 5, 2015 issued in EP 11 760 112.0.
European Office Action dated Jun. 5, 2015 issued in EP 11 836 959.4.
Japanese Office Action [with translation] dated Jun. 23, 2015 issued in JP 2013-536747.
European Examination Report dated Jun. 5, 2015 issued in EP 12 75 2493.
Japanese Office Action dated Oct. 6, 2015 issued in JP 2013-556657.
"Fresnel number," Wikipedia, last modified May 2, 2010, 2pp.
Confocal Raman Microscopy (Oct. 2006) "Optofluidic Microscope Enables Lensless Imaging of Microorganisms," *Biophotonics International*, 13(10):24.
"Zone plate," Wikipedia, last modified Apr. 2, 2009.
Aigouy, L., et al., (2007) "Near-field analysis of surface waves launched at nanoslit apertures," *Physical Review Letters*, 98:153902.
Biener, G., et al., (2011) "Combined reflection and transmission microscope for telemedicine applications infield settings," *Lab Chip*, 11(16):2738-2743.
Blanco et al. (2006) "Microfluidic-optical integrated CMOS compatible devices for label-free biochemical sensing," *J. Micromech. Microeng.* 16:1006-1016.
Borenfreund, E. & Puerner, J. A., (1985) "Toxicity determined in vitro by morphological alterations and neutral red absorption,"*Toxicology Letters* 24:119-124.
Breslauer, D., et al., (Jul. 2009) "Mobile Phone Based Clinical Microscopy for Global Health Applications" *PLoS One*, 4(7):e6320, 7pp.

(56) References Cited

OTHER PUBLICATIONS

Cavanaugh, P.F. et al., (1990) "A semi-automated neutral red based chemosensitivity assay for drug screening," *Investigational new drugs* 8:347-354.

Cohen, A.R., Gomes, F. L.A.F., Roysam, B.& Cayouette, M., (Mar. 2010) "Computational prediction of neural progenitor cell fates," *Nature Methods,* 7(3):213, 10pp.

Costa, M. R. et al., (2011) "Continuous live imaging of adult neural stem cell division and lineage progression in vitro," *Development* 138(6):1057-1068.

Crane, M., Chung, K., Stirman, J. & Lu, H., (2010) "Microfluidics-enabled phenotyping, imaging, and screening of multicellular organisms," *Lab on a Chip* 10:1509-1517.

Denis, L., Lorenz, D., Thiébaut, E., Fournier, C., Trede, D., (2009) "Inline hologram reconstruction with sparsity constraints," *Opt Lett,* 34:3475-3477.

Dykstra, B. et al., (May 23, 2006) "High-resolution video monitoring of hematopoietic stem cells cultured in single-cell arrays identifies new features of self-renewal," *PNAS,* 103(21):8185-8190.

Eilken, H.M., Nishikawa, S.I. & Schroeder, T. (Feb. 2009) "Continuous single-cell imaging of blood generation from haemogenic endothelium," *Nature* 457:896-900.

Farsiu S. et al., (Jan. 2006) "Multiframe Demosaicing and Super-Resolution of Color Images," *IEEE Transactions on Image Processing,* 15(1):141-159.

Farsiu, S., Robinson, D., Elad, M. & Milanfar, P., (2004) "Advances and Challenges in Super Resolution," *International Journal of Imaging Systems and Technology* 14:47-57.

Fienup, J.R., (Jul. 1978) "Reconstruction of an object from the modulus of its Fourier transform," *Opt Lett,* 3(1):27-29.

Garcia-Sucerquia, J., et al., (Feb. 2006) "Digital in-line holographic microscopy," *Appl. Opt.,* 45(5):836-850.

Hardie, R., Barnard, K., and Armsrong, E.E., (Dec. 1997) "Joint MAP Registration and High-Resolution Image Estimation Using a Sequence of Undersampled Images," *IEEE Transactions on Image Processing* 6(12):1621-1633.

Heng, Xin, et al., (2006) "Optofluidic Microscopy—a method for implementing a high resolution optical microscope on a chip," *Lab Chip,* 6(10):1274-1276.

Hou, H., et al., (2010) "Deformability based cell margination—A simple microfluidic design for malaria infected erythrocyte separation," *Lab on a Chip* 10:2605-2613.

Isikman, S.O., et al., (May 3, 2011) "Lens-free optical tomographic microscope with a large imaging volume on a chip," *PNAS USA,* 108(18):7296-7301.

Koren, G., Polack, F., Joyeux, D., (Mar. 1993) Iterative algorithms for twin-image elimination in in-line holography using finite-support constraints, *J Opt Soc Am A* 10:423-433.

Lai, S., King, B., Neifeld, M.A., (2000) "Wave front reconstruction by means of phase-shifting digital in-line holography," *Opt Commun.,* 173:155-160.

Lange et al., (2005) "A microfluidic shadow imaging system for the study of the nematode *Caenorhabditis elegans* in space," *Sensors and Actuators B,* 107:904-914.

Levin-Reisman, I., et al., (2010) "Automated imaging with ScanLag reveals previously undetectable bacterial growth phenotypes," *Nat Meth,* 7(9):737-739.

Li, W., Knoll, T., Thielecke, H., (2010) "On-chip integrated lensless microscopy module for optical monitoring of adherent growing mammalian cells," *Engineering in Medicine and Biology Society (EMBC), 2010 32nd Annual International Conference of the IEEE,* pp. 1012-1015.

Liu, G. and Scott, P., (Jan. 1987) "Phase retrieval and twin-image elimination for in-line Fresnel holograms," *J Opt Soc Am A,* 4(1):159-165.

Malek M., Aliano, D., Coëtmellec, S., Lebrun, D., (May 17, 2004) "Digital in-line holography: Influence of the shadow density on particle field extraction," *Opt. Express,* 12(10):2270-2279.

Medoro, G. et al. (2003) "A Lab-on-a-Chip for Cell Detection and Illumination," *IEEE Sensors Journal,* 3(3):317-325.

Miao, Q., Rahn, J.R., Tourovskaia, A., Meyer, M.G., Neumann, T., Nelson, A.C., and Seibel, E.J., (Dec. 21, 2009) "Dual-modal three dimensional imaging of single cells with isometric high resolution using an optical projection tomography microscope," *J. Biomed. Opt.* 14(6):064034, 6pp.

Micó, V., Garcia, J., Zalevsky, Z., and Javidi, B., (Oct. 2010) "Phase-Shifting Gabor Holographic Microscopy," *J Disp Technol,* 6(10):484-489.

Milanfar, P., (2010) "Super-Resolution Imaging," *CRC Press,* 9pp.

Mudanyali, O., et al., (Jun. 7, 2010) "Compact, light-weight and cost-effective Microscope based on Lensless Incoherent Holography for Telemedicine Applications," *Lab on a Chip,* 10:1417-1428, 25 pp.

Repetto, G., Del Peso, A. & Zurita, J.L., (2008) "Neutral red uptake assay for the estimation of cell viability/cytotoxicity," *Nature Protocols* 3(7):1125-1131.

Rodenburg, J.M., Hurst, A.C., Cullis, A.G., (2007) "Transmission microscopy without lenses for objects of unlimited size," *Ultramicroscopy,* 107:227-231.

Schroeder, T., (2011) "Long-term single-cell imaging of mammalian stem cells," *Nature Methods Supplement* 8(4):S30-S35.

Schultz, R.R., Meng, L., Stevenson, R.L., (1998) "Subpixel motion estimation for superresolution image sequence enhancement," *Journal of Visual Communication and Image Representation,* 9(1):38-50.

Seo, et al., (2009) "Lensfree holographic imaging for on-chip cytometry and diagnostics," *Lab on a Chip,* 9(6):777-787.

Xu, et al. (2001) "Digital in-line holography for biological applications," *PNAS USA,* 98:11301-11305.

Xu, L., Miao, J., Asundi, A., (Dec. 2000) "Properties of digital holography based on in-line configuration," *Opt Eng,* 39(12):3214-3219.

Zhang, F., Pedrini, G., and Osten, W., (2007) "Phase retrieval of arbitrary complex-valued fields through apertureplane modulation," *Phys Rev A,* 75:043805, 4pp.

United States Patent and Trademark Office (USPTO) Final Office Action in U.S. Appl. No. 3/069,651 dated on Mar. 3, 2016.

European Examination Report dated Feb. 2, 2016 issued in EP 12 75 2493.

\* cited by examiner

US 9,343,494 B2

LIGHT GUIDED PIXEL CONFIGURED FOR EMISSIONS DETECTION AND COMPRISING A GUIDE LAYER WITH A WAVELENGTH SELECTIVE FILTER MATERIAL AND A LIGHT DETECTOR LAYER

CROSS-REFERENCES TO RELATED APPLICATIONS

This is a non-provisional application of, and claims priority to, U.S. Provisional Patent Application No. 61/448,964 entitled "Electronic petridish with bright field and fluorescence imaging capabilities for cell culture monitoring," filed on Mar. 3, 2011. This provisional application is hereby incorporated by reference in its entirety for all purposes.

This non-provisional application is related to the following co-pending and commonly-assigned patent application, which is hereby incorporated by reference in its entirety for all purposes: U.S. patent application Ser. No. 13/281,287 entitled "Scanning Projective Lensless Microscope System," filed on Oct. 25, 2011.

The following non-provisional application is being filed on the same day and is hereby incorporated by reference in its entirety for all purposes: U.S. patent application Ser. No. 13/411,302 entitled "e-Petri Dishes, Devices, and Systems," filed on Mar. 2, 2012.

STATEMENT AS TO RIGHTS TO INVENTIONS MADE UNDER FEDERALLY SPONSORED RESEARCH OR DEVELOPMENT

This invention was made with government support under Grant No. AIO96226 awarded by the National Institutes of Health. The government has certain rights in the invention.

BACKGROUND OF THE INVENTION

Embodiments of the present invention generally relate to imagers and sensors. More specifically, certain embodiments relate to light guided pixels, light guided pixel devices, and light guided pixel systems for bright field and fluorescence/phosphorescence imaging.

In addition to bright field imaging, fluorescence/phosphorescence imaging can be crucial to study or monitor structural and functional morphology of biological samples in biomedicine and biological sciences. For example, fluorescence/phosphorescence imaging techniques can be used to identify or detect microscopic structures, submicroscopic structures, even individual molecules in biological samples.

Conventional fluorescence microscopes are common tools that use fluorescence imaging to investigate biological problems. Typically, a fluorescence/phosphorescence dye is mixed with a specimen to mark or tag portions of the specimen(s) (e.g., cell(s)) under investigation with fluorophore(s). A fluorophore refers to a component of a molecule that causes the molecule to fluorescence or phosphorescence once excited. A fluorophore can absorb energy from excitation light of a specific wavelength(s) and re-emit the energy at a different wavelength(s). The conventional fluorescence microscope irradiates the sample with excitation light of predetermined wavelength(s) (e.g., blue light) to activate fluorophore(s) in the sample. In response, fluorophore(s) release fluorescence/phosphorescence emissions of different wavelength(s) (e.g., green light). The emissions are usually much weaker than the excitation light and are scattered from each fluorophore.

Most conventional fluorescence microscopes have a filter between the sample and the detector surface. The filter absorbs or reflects the excitation light and passes the weaker fluorescence/phosphorescence emissions of different wavelengths to the sensor. When using conventional absorptive dyes, the filter may be designed with a thickness of more than a few micrometers due to attenuation coefficients. The diffraction, interference, and scattering of the weak emission signal within the filter can degrade resolution of the fluorescence images.

BRIEF SUMMARY OF THE INVENTION

Embodiments of the present invention relate to light guided pixels, light guided pixel devices, and light guided pixel systems for bright field and fluorescent/phosphorescent emission detection and imaging. A light guided pixel device includes a guide layer with light guides (e.g., metal grid) over a light detector layer (e.g., CMOS image sensor). Each light guide channels light toward a corresponding light detecting element(s) in the light detector layer. Each light guide may include a filter for channeling emissions to the light detecting element(s). Channeling the light (e.g., emissions) can improve resolution by confining propagation of the light signal. The inter-pixel separation between light guides can also improve resolution by reducing overlap of the signal between neighboring light detecting elements.

One embodiment is directed to a light guided pixel including a guide layer with a light guide for channeling light. The light guided pixel also includes a light detector layer having a light detecting element that receives light channeled by the light guide.

Another embodiment is directed to a light guided pixel device comprising a guide layer and a light detector layer. The guide layer has a plurality of light guides. The light detector layer has a plurality of light detecting elements. Each light guide is configured to receive light channeled by a corresponding light guide of the plurality of light guides.

Another embodiment is directed to a light guided pixel system comprising a light guided pixel device and a processor. The light guided pixel device has a guide layer and a light detector layer. The guide layer has a plurality of light guides. The light detector layer has a plurality of light detecting elements. Each light detecting element is configured to receive light channeled by a corresponding light guide of the plurality of light guides. The processor is in communication with the plurality of light detecting elements. The processor is configured to generate one or more projection images of a specimen located between an illumination source and the guide layer based on light received by the plurality of light detecting elements.

Another embodiment is directed to a light guided pixel system comprising a guide layer, a light detector layer, an array of light guided pixels, and a processor. The guide layer has a plurality of light guides. The light detector layer has a plurality of light detecting elements. Each light guided pixel comprises a light guide of the plurality of light guides and a corresponding light detecting element of the plurality of light detecting elements. The light detecting element is configured to receive light channeled from the corresponding light guide. The processor is configured to generate one or more projection images of a specimen located between an illumination source and the guide layer based on light received by the plurality of light detecting elements.

These and other embodiments of the invention are described in further detail below.

DETAILED DESCRIPTION OF THE INVENTION

Figure 1:
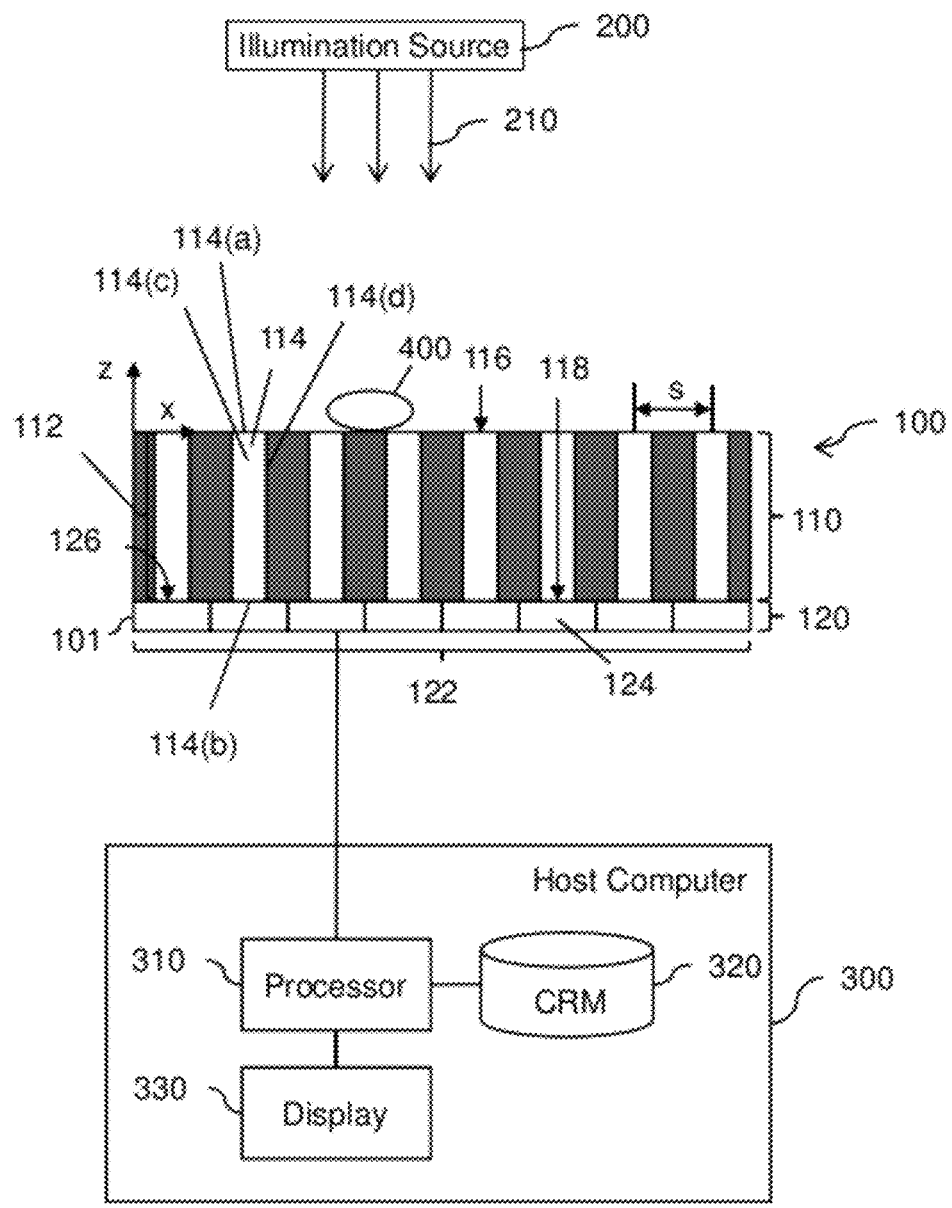
FIG. 1 a block diagram of a light guided pixel system, according to embodiments of the invention.

Embodiments of the present invention will be described below with reference to the accompanying drawings. Embodiments are directed to a light guided pixel device having a guide layer with a plurality of light guides and a light detector layer with a plurality of light detecting elements (e.g., image sensor pixels). Each light guide channels light toward a corresponding light detecting element(s) in the light detector layer. In one case, each light detecting element of the plurality of light detecting elements receives light from a single light guide. The light guides may also include a filter to reject excitation light and pass emissions. By channeling light from a location near the specimen, the light guides may reduce scattering, diffraction, and diffusion, which can improve resolution. The inter-pixel separation between the light guides may further improve resolution by separating light from each light guide to reduce overlap to neighboring light detecting elements.

In operation, an illumination source provides illumination (e.g., scanning illumination, focal spot illumination, etc.) to a specimen outside the guide layer. The specimen alters the light. The light guides channel altered light (e.g., emissions) and unaltered light (e.g., excitation light) to the corresponding light detecting elements. The plurality of light detecting elements measure the light channeled through the plurality of light guides. A processor can generate an image of the specimen based on the light channeled through the light guides. In one case, the illumination source sweeps illumination from multiple scanning locations to generate a sequence of sub-pixel shifted projections on the light detector surface. In this case, the processor can generate a high resolution (i.e. sub-pixel resolution) image of the specimen based on the sequence of sub-shifted projections. In another case, the illumination source scans a focal spot array providing excitation light over a specimen to locally excite fluorophores. In this case, the processor can generate a high resolution fluorescence image. By using light guides, the light guided pixel device relays the in-focus plane from the detector surface to the outer surface of the guide layer. This relay allows the light guided pixel device to achieve high resolution bright-field imaging and/or fluorescence imaging of the specimen even with the existence of an additional layer (e.g. filter) between the specimen and the light detector.

Embodiments of the invention provide one or more technical advantages and improvements. An advantage is the improvement of image resolution. The light guides channel light from locations near the specimen and can confine propagation of light signal, which can improve resolution. The inter-pixel separation between the light guides may further improve resolution by keeping light from each light guide separate to reduce overlap to neighboring light detecting elements. Another advantage is that the light guided pixel device can be an on-chip device. An on-chip light guided pixel device can provide a compact imaging platform for both bright-field and fluorescence high-resolution imaging of biological samples, rendering it a powerful tool in biological and medical studies.

I. Light Guided Pixel System

FIG. 1 is a diagram of a light guided pixel system 10, according to embodiments of the invention. The light guided pixel system 10 includes a light guided pixel device 100 having a body 101 with a guide layer 110 (e.g., metal grid) and a light detector layer 120. The guide layer 110 includes a plurality of light guides 112 having eight discrete light guides 114 separated by an inter-pixel separation, s. A light guide 114 can refer to any suitable structure or combinations of structures capable of channeling light. In FIG. 1, each light guide 114 includes a first end 114(a), a second end 114(b), a light transmissive region (core) 114(c), and a reflective surface 114(d). In this example, each light guide 114 can channel light toward the second end 114(b). The guide layer 110 also includes an outer surface 116 and an inner surface 118. The light detector layer 120 includes a plurality of light detecting elements 122 (e.g., CMOS image sensor pixels) having eight discrete light detecting elements 124 (e.g., sensor pixels). The light detector layer 120 has a detector surface 126, which is coincident in this embodiment with the inner surface 118 of the guide layer 110.

The light guided pixel device 100 in FIG. 1 also includes an x-axis, a y-axis (not shown), and a z-axis. The x-axis and y-axis lie in a plane at the outer surface 116 of the guide layer 110. The z-axis is orthogonal to this plane. Although the light guided pixel device 100 in the illustrated example includes eight discrete light guides 114 in the x-direction corresponding to eight light detecting elements 122 in the x-direction, other embodiments may include any suitable number (e.g., 1, 5, 10, 100, 1000, etc.) of discrete light detecting elements 124 and/or light guides 114 in the x-direction and/or y-direction.

The light guided pixel system 10 also includes an illumination source 200 providing illumination 210. In addition, the light guided pixel system 10 includes a host computer 300 having a processor 310, a computer readable medium (CRM)

320, and a display 330. The display 330 and the CRM 320 are in communication with the processor 310. The processor 310 is in communication with the light detector layer 120 of the light guided pixel device 100. Although a single light guided pixel device 100 is shown in FIG. 1, a light guided pixel system 10 of other embodiments may include multiple light guided pixel devices 100. An optional relay multiplexer in communication between the multiple light guided pixel devices 100 and the processor 310 can be used to relay information from the multiple light guided pixel devices 100 to the processor 310.

In operation, the illumination source 200 provides illumination 210 to a specimen 400 located between the illumination source 200 and the guide layer 110. The specimen 400 alters the illumination 210 (e.g., absorbs excitation light and re-emit light from activated fluorophores), which generates a projection on the outer surface 116 of the guide layer 110. The plurality of light guides 112 receives altered and unaltered light. Each of the light guides 114 channels light toward the light detector surface 126. The plurality of light detecting elements 122 measure light received through the plurality of light guides 112. The processor 310 can generate an image of the specimen 400 based on the measured light through the plurality of light guides 112. In one scheme, the illumination source 200 may sweep the illumination 210 from multiple scanning locations to generate a sequence of sub-pixel shifted projections of the specimen 400 at the outer surface 116. In this case, the processor 310 can generate a high resolution (i.e. sub-pixel resolution) image of the specimen 400 based on the sequence of sub-pixel shifted projections. In another scheme, the illumination source 200 may provide illumination 210 in the form of an array of light focus spots for exciting fluorophores in the specimen 400 near each focus spot. The array of focus spots can be scanned over the specimen 400. In this scheme, the processor 310 can generate a high resolution (i.e. sub-pixel resolution) fluorescence image of the specimen 400 based on the light received through the plurality of light guides 112.

Figure 2:
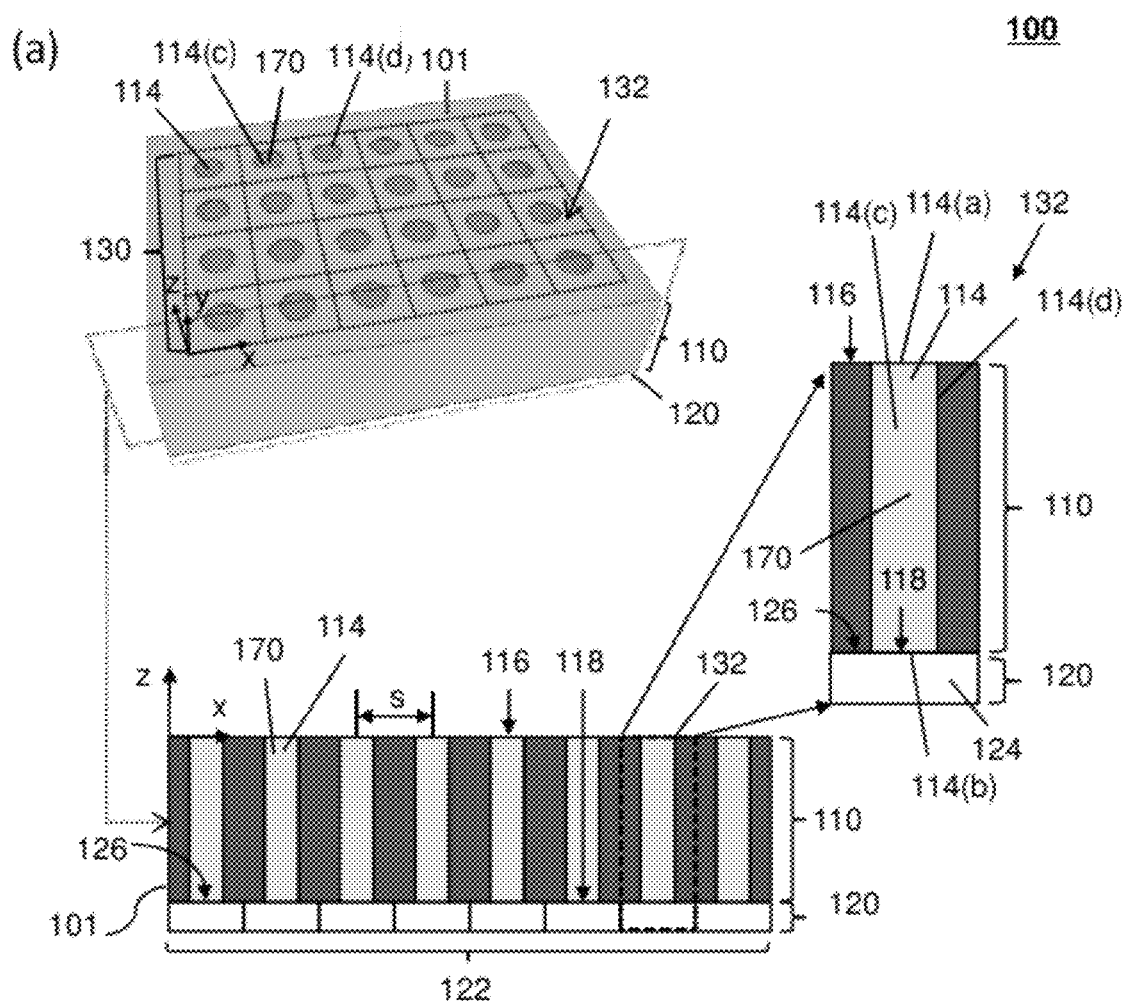
FIG. 2(a) are schematic drawings of perspective and cross-sectional views of a light guided pixel device having an array of light guided pixels, and a cross sectional view of a single light guided pixel, according to an embodiment.
FIG. 2(b) is a transparency perspective view of the light guided pixel device of FIG. 2(a), according to the embodiment.
Figure 2:
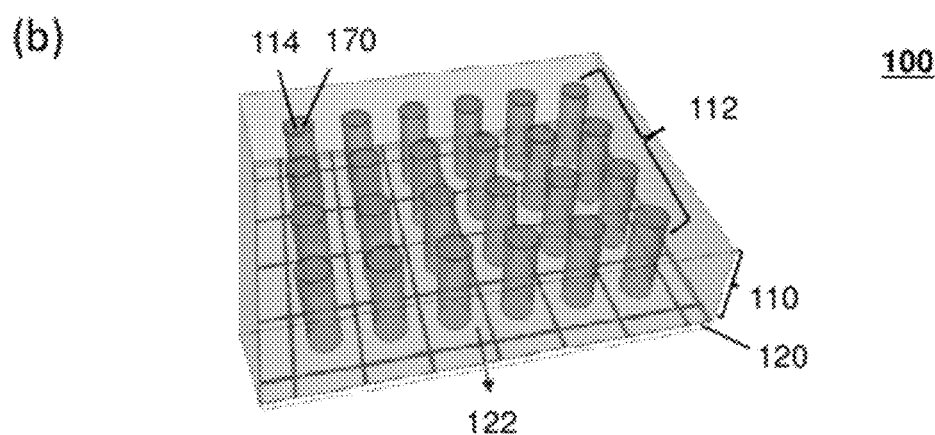

FIG. 2(a) are schematic drawings of perspective and cross-sectional views of a light guided pixel device 100 having an array of light guided pixels 132, and a cross sectional view of a single light guided pixel 132, according to an embodiment. FIG. 2(b) is a transparency perspective view of the light guided pixel device 100 of FIG. 2(a), according to the embodiment.

In FIGS. 2(a) and 2(b), the light guided pixel device 100 has a body 100 comprising a guide layer 110 and a light detector layer 120. The guide layer 110 includes a plurality of light guides 112 in the form of a 6×4 array of 24 discrete light guides 114. The guide layer 110 also includes an outer surface 116 and an inner surface 118. The light detector layer 120 includes a plurality of light detecting elements 122 in the form of a 6×4 array of 24 discrete light detecting elements 124. The light detector layer 120 also includes a detector surface 126, which is coincident in this embodiment with the inner surface 118 of the guide layer 110. The light guided pixel device 100 also includes an x-axis, a y-axis, and a z-axis. The x-axis and y-axis lie in a plane at the outer surface 116 of the guide layer 110. The z-axis is orthogonal to this plane.

The body 101 of the light guided pixel device 100 in FIGS. 2(a) and 2(b) also includes a two-dimensional array of discrete light guided pixels 130. The two-dimensional array is a 6×4 array of 24 discrete light-guided pixels 132. In other embodiments, the light guided pixel device 100 may include a two-dimension array of another suitable dimension ((e.g., 10×100, 100×100, 1000×20, 1000×1000, etc.). The array of light guided pixels 130 has an inter-pixel separation, s, between adjacent light guided pixels 132.

A light guided pixel 132 can refer to a structure, device or combination thereof that includes a single light guide 114 and one or more light detecting elements 124 configured to receive light channeled from the single light guide 114. In FIGS. 2(a) and 2(b), each light guided pixel 132 includes a guide layer 110 with a single light guide 114. Each light guide 114 includes a first end 114(a), a second end 114(b), a light transmissive region (core) 114(c), and a reflective surface 114(d) having a cylindrical shape. The light guide 114 can channel light toward the second end 114(b). In this example, the light transmissive region 114(c) has a filter 170 for rejecting excitation light and passing emissions from activated fluorophores in a specimen 400 (not shown) between the illumination source 200 and the guide layer 110.

In a fluorescence/phosphorescence imaging schemes of the light guided pixel device 100 in FIGS. 2(a) and 2(b), an illumination source 200 outside the guide layer 110 provides illumination 210 of excitation light to a specimen 400 (not shown) located between the illumination source 200 and the guide layer 110. Fluorophores in the specimen 400 absorb the excitation light and re-emit light of a different wavelength(s) (emissions). The light guides 112 receive light altered and unaltered by the specimen 400. The filter 170 in the light guides 112 reject the excitation light and pass emissions. The plurality of light detecting elements 122 measure emissions channeled through the plurality of light guides 122. A processor 310 (shown in FIG. 1) can generate a fluorescence image of the specimen 400 based on the emissions measured by the plurality of light detecting elements 122.

Figure 3:
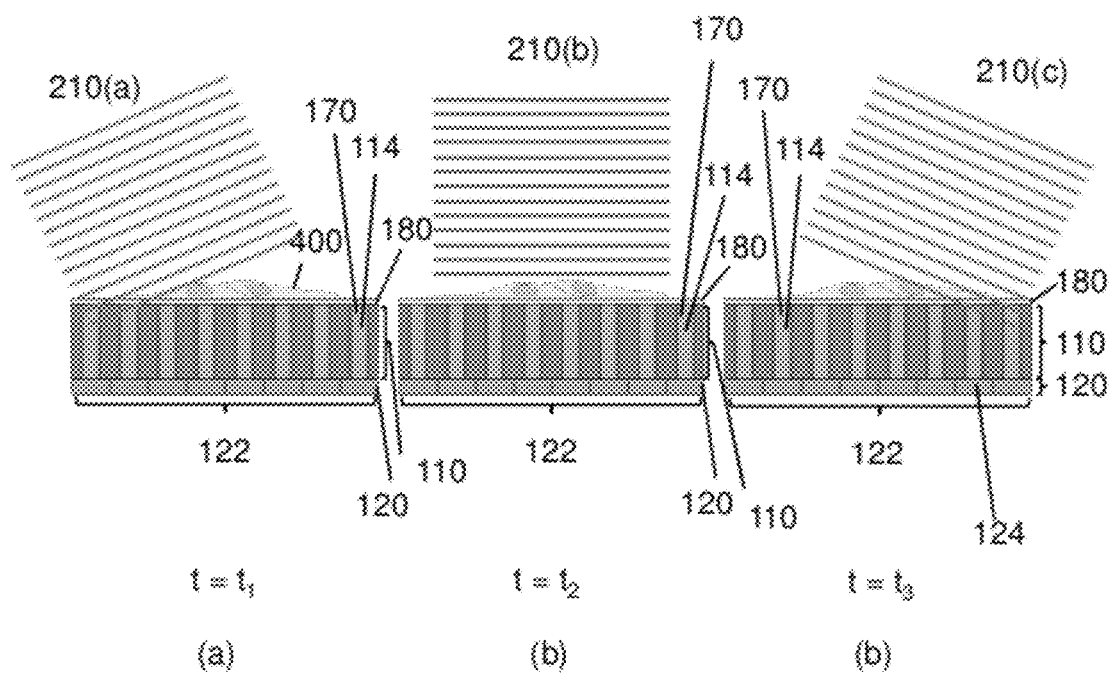
FIGS. 3(a), 3(b), and 3(c) are schematic drawings of components of a light guided pixel device during an exemplary bright-field high-resolution imaging scheme, according to an embodiment of the invention.

In embodiments, a body 101 can refer to a multi-layered or monolithic structure. The body 101 may include any suitable device (e.g., a light guide 114, a light detecting element 124, filter 170, etc.) or combination of devices. In illustrated examples such as the example in FIG. 1, the body 101 is a multi-layered structure comprising a guide layer 110 and a detector layer 120. Each layer of the multi-layer body 101 of these embodiments may have any suitable thickness and may have any suitable sublayers. Although some embodiments of the light guided pixel device 100 may have a multi-layer body 101 with certain layers, other embodiments may integrate, omit, or add one or more layers or change the location of one or more layers. For example, a multi-layer body 101 of an embodiment may include a coating on the outer surface 116 that is made of a bio-compatible material for cells and other specimens 400 to be able to attach and grow well. As another example, a multi-layer body 101 of an embodiment may include an additional transparent layer between the light detector layer 120 and the guide layer 110. As another example, a multi-layer body 101 of an embodiment may include an additional transparent layer 180 (shown in FIGS. 3, 4, and 5) outside the outer surface 116 of the guide layer 110. Semiconductor and/or micro/nanofabrication procedures may be used to locate one or more layers of a multi-layered body 110.

A guide layer 110 can refer to a layer having one or more light guides 114. The light guides 114 may be defined by or included in the guide layer 110. The portion of the guide layer 110 between the light guides 114 may be made of any material that can block the light from crossing over between adjacent light guides 114. For example, the material may be a reflective metal or other opaque reflective material, a material coated with thin reflective metal layer, or a material with a lower refractive index than the material of the light transmissive region 114(c) (e.g., fiber optic faceplates). The guide layer 110 may have any suitable thickness. In one case, the guide layer 110 may have a thickness that is large enough to attenuate the background excitation light and that provides a high enough signal-to-background ratio for the light detector to measure the emission signal.

A light guide 114 can have any suitable structure or combinations of structures capable of channeling light. In embodiments, a light guide 114 may include a first end 114(a), a second end 114(b) proximal the light detector layer 120, a light transmissive region (core) 114(c) between the first end 114(a) and the second end 114(b), and one or more reflective surfaces 114(d) proximal the light transmissive region 114(c) and between first end 114(a) and the second end 114(b). In these embodiments, light may be channeled toward the second end 114(b) by reflecting from the one or more reflective surfaces 114(d).

The light transmissive region 114(c) can be made of any suitable material. The light transmissive region 114(c) may be a void, may be a partial void that is partially filled with material, or may be completed filled with material. In some cases, the light transmissive region 114(c) may include a void defined by the one or more reflective surfaces 114(d). In other cases, the light transmissive region 114(c) may include material between the one or more reflective surfaces 114(d).

The light guide 114 includes one or more reflective surfaces 114(d). In one case, the one or more reflective surfaces 114(d) may be the one or more surfaces formed in a guide layer 110 made of a reflective material. For example, the one or more reflective surfaces 114(d) may be a single outer cylindrical surface of a cylindrical hole formed in metallic guide layer 110. In another case, the one or more reflective surfaces 114(d) may be the one or more surfaces of a reflective coating covering the one or more surfaces formed in a guide layer 110 in the guide layer 110. In another case, the one or more reflective surfaces 114(d) may be formed by the interface between a light transmissive region 114(c) of a first dielectric material and portion of the a guide layer 110 between the light guides 114 made of another dielectric material with a lower refractive index. An example of such a light guide 114 may be an optical fiber.

The one or more reflective surfaces 114(d) may have any suitable shape and size. In some cases, the reflective surface 114(d) may have a constant cross-sectional shape (e.g., a circle, rectangle, triangle, oval, etc.) and size from the first end 114(a) to the second end 114(b). In FIG. 1, for example, the reflective surface 114(d) of the light guides 114 is a cylindrical surface having a constant diameter. In other examples, the cross-sectional shape and/or size may vary from the first end 114(a) to the second end 114(b). For example, the reflective surface 114(d) may be conical. The dimensions (e.g., diameter, width, etc.) of the reflective surface 114(d) of the light guide 114 of embodiments may have any suitable value (e.g., 0.50 micron, 1 micron, 3 microns, 6 microns, 10 microns, etc.). In some cases, the light guide 114 may be sized to be a fraction of the size (e.g., pixel size) of the corresponding light detecting element(s) 124 (e.g., 1-10 microns) to reduce overlap to neighboring light detecting elements 124.

The light guide(s) 114 of embodiments may have any suitable location relative to the corresponding light detecting element(s) 124 and any suitable orientation (e.g., a z-directional orientation or slanted orientation). In FIG. 1, each light guide 114 is oriented in the z-direction and is centered about the center of a single light detecting element 122. With this location and orientation, the light guide 114 can channel light out the second end 114(b) and generally toward the center of the single corresponding light detecting element 122. In other embodiments, a light guide 114 may be centered about the center of two or more light detecting elements 122. In other embodiments, a light guide 114 may be oriented at an angle from the z-axis to channel light at an angle.

The cross sectional shape of the light guides 114 can vary from straight column, slanted column and frustum (cut off cone or pyramid) in some embodiments. Also, the arrangement of the light guides 114 can also vary between many different shapes, and is determined by the photomask pattern used during the fabrication process. Depending on the type of illumination 210 and the height of the light guided pixels 132, different shapes may result in different collection efficiencies of fluorescent light and/or higher excitation light rejection.

In embodiments, one or more light guides 114 of the light guided pixel device 100 may include a filter 170 (as shown in FIG. 2(a)). A filter 170 can refer to any suitable optical filter material (e.g., absorptive color dye, multiple dielectric layers) that can selectively reject (e.g., absorb or reflect) light of certain wavelengths (i.e. excitation light) from the illumination source 200 and allows light of other wavelengths (e.g., light including emissions) to be directed through the light guide 114. In embodiments, a filter 170 may be a material that can reject illumination 210 of excitation light having a narrow bandwidth provided by the illumination source 200 and pass light of other wavelengths including emissions from fluorophores in the specimen 400 activated by the excitation light. For example, the illumination source 200 may provide illumination 210 of blue excitation light to excite fluorophores in the specimen 400. The fluorophores may emit green light in response. The filter 170 in the light guide 114 may be a green filter that can screen out the blue excitation light from the illumination source 200 and allows the green emissions to pass to the light detecting elements 124. Although illustrated embodiments include a single filter 170 in the light guide 114, other embodiments may include multiple filters in the light guide 114.

In embodiments such as the one shown in FIG. 1, the guide layer 110 includes a plurality of light guides 112. The plurality of light guides 112 may have any suitable number (e.g., 1, 3, 6, 8, 10, 100, etc.) of light guides 114 and may be in any suitable arrangement (e.g., one-dimensional array, two-dimensional array, combination of one-dimensional and two-dimensional arrays). The plurality of light guides 112 may be oriented in any suitable direction in the guide layer 110. In FIG. 1, the plurality of light guides 112 is oriented in the x-direction. The plurality of light guides 112 has an inter-pixel separation, s, which is defined as the distance in the x-y plane between the central axes of two neighboring light guides 114 in the plurality of light guides 112.

A light detector layer 120 can refer to a layer which includes devices (e.g., light detecting elements 124), structures (e.g., sublayers of material), or combinations thereof, that are capable of receiving light and generating signal(s) with light data based on light received. The signal(s) may be in the form of electrical current from the photoelectric effect. In some embodiments, the light detector layer 120 may comprise a plurality of sublayers (e.g., passivation sublayer, microlens sublayer, filter sublayer, active photosensitive sublayer, protective outer sublayer, etc.). For example, the light detector layer 120 may include an outside passivation sublayer, an inner microlens sublayer, and an inside active photosensitive sublayer. As another example, the light detector layer 120 may include only an active photosensitive layer. In this example, the light detector layer 120 may be fabricated by removing the color filter and microlens sublayers from a pre-fabricated imaging sensor. The color filter and microlens sublayers may be removed by treating the pre-fabricated imaging sensor under oxygen plasma for a period of time (e.g., 10 minutes at 80 W).

In embodiments, the light detector layer 120 includes one or more discrete light detecting elements 124. The light detecting elements 124 may be arranged in any suitable form such as a single light detecting element 124, a one-dimensional array of light detecting elements 124, a two-dimensional array of light detecting elements 124, or a multiplicity of one-dimensional and/or two-dimensional arrays of light detecting elements 124. Some examples of suitable arrays include a complementary metal oxide semiconductor (CMOS) array, an avalanche photo-diode (APD) array, a charge coupled device (CCD) array, a photo-diode (PD) array, a photomultiplier tubes (PMT) array, and other suitable arrays. These arrays and others are commercially available. The light detecting elements 124 may be monochromatic detectors or color detectors (e.g., RGB detectors). The light detecting elements 124 may be of any suitable size (e.g., 1-10 microns) and any suitable shape (e.g., circular, rectangular, square, etc.). For example, a light detecting element 124 of a CMOS or CCD array may be 1-10 microns and a light detecting element 124 of an APD or PMT array may be as large as 1-4 mm.

Light data refers to any suitable information related to light received by a light detecting element 124. Light data may include, for example, information about the properties of the light detected such as the intensity of the light, the wavelength(s) of the light, the frequency or frequencies of the light, the polarization(s) of the light, the phase(s) of the light, the spin angular momentum(s) of the light, and/or other light properties associated with the light received by the light detecting element 124. Light data may also include the location of the light detecting element 120(a) receiving the light and generating a specific signal. The light data may also include the time that the light was detected by a particular light detecting element 124. Light data may be data based on a single (sample) time, based on multiple (sample) times, or based on a time-varying basis. In some cases, the light data may include emissions data, which is light data associated with emissions received by one or more light detecting elements 124.

In embodiments, the light detector layer 120 (e.g., photosensor) includes a plurality of discrete light detecting elements 122 (e.g., sensor pixels) for receiving light channeled through the plurality of light guides 112 in the guide layer 110. The plurality of light detecting elements 122 may include any suitable number (1, 2, 4, 10, 16, 100, 1000, etc.) of light detecting elements 124. The plurality of light detecting elements 122 may be a portion or a two-dimensional array of light detecting elements 124 in the light detecting layer 120. In FIGS. 2(a) and 2(b), the light detector layer 120 includes a plurality of light detecting elements 122 that is an entire two-dimensional array of light detecting elements 124. In one embodiment, the plurality of light detecting elements 122 may be a portion of a two-dimensional array of light detecting elements 124 and another portion of the two-dimensional array of light detecting elements may be covered by the guide layer 110 in order to expand the inter-pixel separation between light guides 114.

In FIG. 1 and other embodiments, each of the light detecting elements 124 in the plurality of light detecting elements 122 uniquely corresponds to a single light guide 114. In these examples, each of the light detecting elements 124 can generally only receive light channeled from the corresponding single light guide 114. In other embodiments, multiple light detecting elements 124 in the plurality of light detecting elements 122 may correspond to a single light guide 114. In these embodiments, the multiple light detecting elements 124 can generally only receive light from the corresponding light guide 114.

In FIG. 1 and other embodiments, the specimen 400 being examined (e.g., imaged) by the light guided pixel device 100 is a single object (e.g., cell) located on the outer surface 116 of the guide layer 110. Although a single object is shown in illustrated embodiments, in other embodiments the specimen 400 being examined may include any suitable number (e.g., 1, 2, 10, 100, 1000, etc.) of objects. The specimen 400 being examined by the light guided pixel device 100 of embodiments may include any suitable type(s) of object(s) such as, for example, biological or inorganic entities. Examples of biological entities include cells, cell components (e.g., proteins), microorganisms such as bacteria or viruses, etc.

Figure 7:
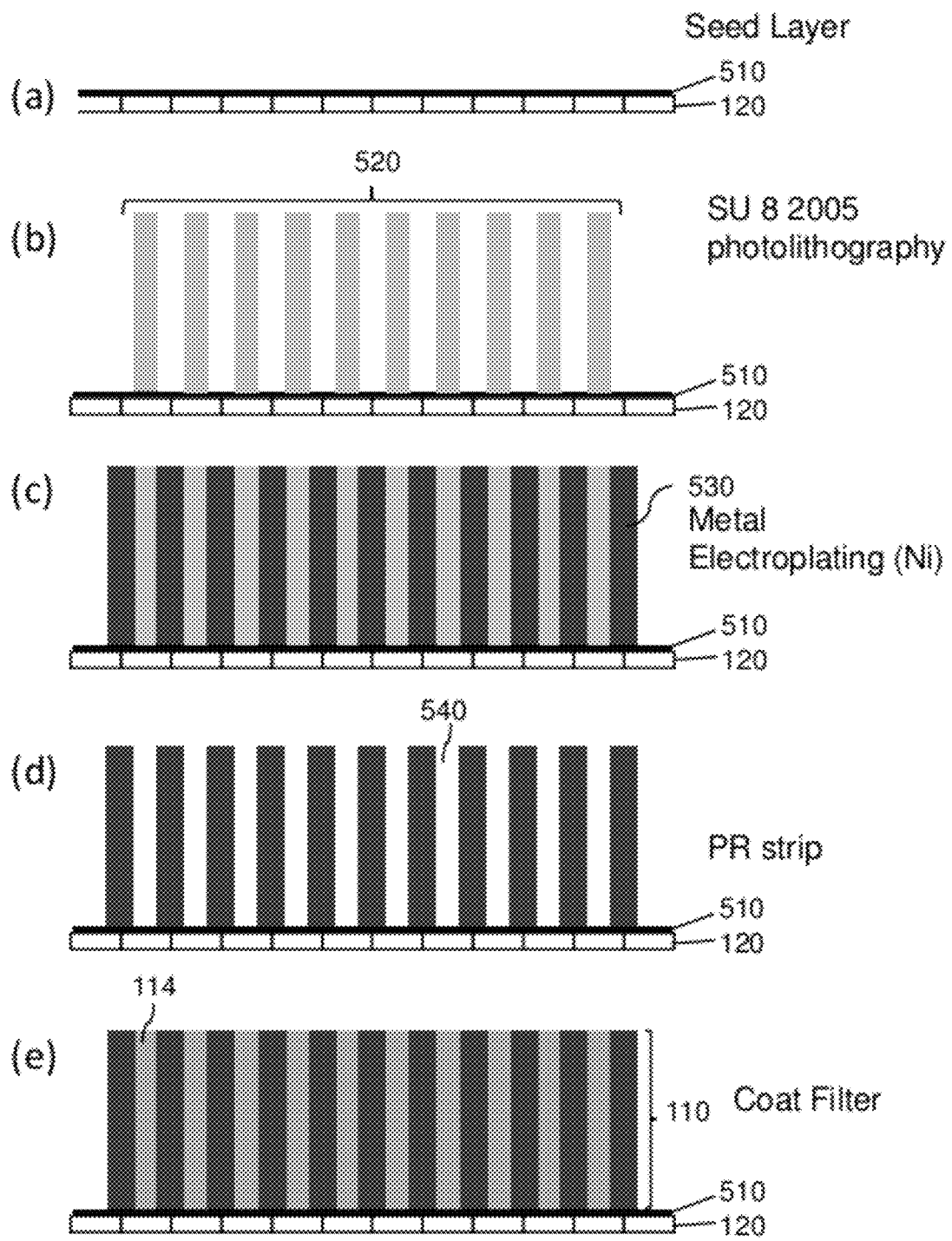
FIG. 7 is a schematic drawing of steps of a LIGA process that may be used to fabricate a body of a light guided pixel device, according to an embodiment of the invention

In FIG. 1, the light guided pixel system 10 includes an illumination source 200. In other embodiments, the illumination source 200 may be separate from the light guided pixel system 10. An illumination source 200 refers to any suitable device/structures, combination of devices/structures, or other suitable source of light (e.g. ambient light, thermal sources, etc.) capable of providing illumination 210 to the specimen 400. Suitable devices and structures may be naturally and/or commercially available. Some examples of suitable structures include an aperture, an aperture array, a holographic plate generating array of focal spots, a focus array generator, and other suitable structures. For example, the illumination source 200 may provide light through an aperture to a local area of the specimen 400. In another example, the illumination source 200 may include a metal probe to provide light to a local area of the sample as shown in FIG. 7. In another example, the illumination source 200 may include a focused beam array generator to generate a focused beam array. In another example, the illumination source 200 may include a holographic plate to generate an array of focal spots. Some examples of suitable devices may include thermal sources, LEDs, continuous-wave lasers, pulsed lasers, etc. The illumination source 200 may be placed in any suitable location and/or may include suitable components (e.g., reflective surfaces, lens, aperture array, etc.) to direct illumination 200 to the specimen 400 as required.

The illumination source 200 provides illumination 210 having properties (e.g., wavelengths, intensities, polarizations, phases, etc.) suitable for the desired imaging scheme. The illumination 210 may be continuous or time-gated by, for example, a pulsed laser (e.g., mode locked lasers, Q switch lasers, etc.). The illumination 210 may be in any suitable form (e.g., one or more beams, an array of focal spots, a light field, an interference pattern generated by multiple of coherent light sources, etc.).

In a fluorescence imaging scheme, the illumination source 200 may provide illumination 210 with excitation light. Excitation light can refer to light having a specific wavelength or narrow bandwidth of wavelengths capable of activating fluorophores in the specimen 400 being examined The specific wavelength or narrow bandwidth of wavelengths may be based on the excitation spectrum of the fluorescence dye used. Some examples of suitable illumination sources that can be used in a fluorescence imaging scheme include lasers, LEDs, etc. In some cases, a holographic plate or other suitable structure may be used to generate an array of focal spots for providing illumination 210.

In one embodiment, the illumination source 200 may be a scanning illumination source capable of providing illumination 210 from different scanning locations at different times. The scanning can be accomplished using various methods that may involve, for example, scanning stages or mirrors, LED arrays, a flat panel display screen, or other suitable devices. In one example, the illumination source 200 may be a device (e.g., smartphone) having a display (e.g., LCD) with a light element (e.g., set of one or more display pixels) that can translate (shift) to different scanning locations across the display in order to provide illumination 210 from different scanning locations at different times ($t=t_1$, $t_{,2}$, $t_3$, etc.). The shifting light element may provide illumination 210 to the specimen 400 from different illumination angles at different times to generate shifting projections of the specimen 400 on the outer surface 116. As another example, the illumination source 200 may include a holographic plate or differential optical element or other structure capable of generating an array of focus spots. In this example, the illumination source 200 may also include a scanning mechanism (e.g., raster scanner) to scan the array of focal spots across the specimen 400 providing illumination 210 at different illumination spots on the specimen 400 on a time varying basis.

The light guided pixel system 10 of FIG. 1 includes a host computer 300 communicatively coupled to the light detector 120. The host computer 300 comprises a processor 310 communicatively coupled to a CRM 320 and a display 330. Alternatively, the host computer 300 can be a separate device from the light guided pixel system 10. The host computer 300 can be any suitable computing device such as a smart-phone, tablet, etc.

In FIG. 1, the processor 310 (e.g., microprocessor) receives signal(s) with light data (e.g., emissions data) from the light detector 120 associated with light received by the plurality of light detecting elements 122. The processor 310 can analyze the light data. In some cases, the processor 310 can generate image data associated with the specimen 400 based on the light data received from the light detector 120. Image data refers to any suitable data that can be used to generate an image of a portion of the specimen 400 on the display 330 or other suitable output device.

The light guided pixel system 10 of embodiments can generate bright-field and/or fluorescence images of the specimen 400 or a portion of the specimen 400. For example, the light guided pixel system 10 of an embodiment may generate a bright-field and fluorescence image of a single object (e.g., cell or cell component) in a multi-object specimen 400. The light guided pixel system 10 of embodiments can generate high resolution images (e.g., sub-pixel resolution images) and/or low resolution images. The light guided pixel system 10 of embodiments can generate color and/or black and white images.

The processor 310 executes code stored on the CRM 320 to perform some of the functions of light guided pixel system 10. Some suitable functions of the light guided pixel system 10 include interpreting emissions data and other light data, performing analyses of the emissions data and other light data, generating fluorescence image data using emissions data, generating bright-field image data from other light data, generating a high-resolution image based on a sequence of sub-pixel shifted projection images, etc.

The CRM (e.g., memory) 320 stores code for performing some functions of the light guided pixel system 10. The code is executable by the processor 310. In embodiments, the CRM 320 may comprise: a) code for interpreting emission data and other light data received from the light detector 120, b) code for generating fluorescence image data of the specimen 400 using emissions data, b) code for generating bright-field image data of the specimen 400 based on light data, c) code for generating an image on the display 330 based on the image data, d) code for generating a high-resolution image of the specimen 400 based on a sequence of sub-pixel shifted projection images of the specimen 400, f) and/or any other suitable code for performing functions of the light guided pixel system 10. The CRM 320 may also include code for performing any of the signal processing or other software-related functions that may be created by those of ordinary skill in the art. The code may be in any suitable programming language including C, C++, Pascal, etc.

The light guided pixel system 10 also includes a display 330 communicatively coupled to the processor 310. Any suitable display may be used. In one embodiment, the display may be a part of the DEDD 100. The display 330 may provide analysis results (e.g., a fluorescence image of an object in the specimen 400) being examined to a user of the light guided pixel system 10.

In one embodiment, a light guided pixel device 100 may have a guide layer with a first plurality of light guides and a second plurality of light guides. The first plurality and second plurality of light guides may be interspersed with each other. The light guides 114 of the first plurality of light guides may have a filter and the light guides 114 of the second plurality of light guides may not have a filter. The light guided pixel device 100 may have a light detecting layer 120 having a first plurality of light detecting elements 122 receiving light channeled through the first plurality of light guides 112 and a second plurality of light detecting elements 122 receiving light channeled through the second plurality of light guides 112. The first plurality of light detecting elements 122 can receive light which could be used by the processor to generate a bright field image of the specimen. At the same time, the second set of light detecting elements 122 can receive light which can be used to generate a fluorescence/phosphorescence image of the specimen.

Modifications, additions, or omissions may be made to light guided pixel system 10 without departing from the scope of the disclosure. In addition, the components of light guided pixel system 10 may be integrated or separated according to particular needs. For example, the processor 310 or other suitable processor may be integrated into the plurality of light detecting elements 124. As another example, the processor 310 and CRM 320 may be components of a computer (e.g., cloud computer) separate from the light guided pixel system 10 and in communication with the light guided pixel system 10. As another example, the light guided pixel device 100 of embodiments may include a stage or other container for holding the specimen 400 while the specimen 400 is being examined.

II. Imaging Schemes

Both bright field and/or fluorescence imaging can be accomplished with the light guided pixel system 10 using the light guided pixel device 100 of FIGS. 2(a) and 2(b). For bright field imaging, the illumination source 200 can scan (e.g., raster scan) illumination 210 to a plurality of scanning locations at different scanning times. The plurality of scanning locations may be designed to generate a sequence of sub-pixel shifted projections of the specimen 400 on the outer surface 116 of the guide layer 110. In a sequence of sub-pixel shifted projections, adjacent projections are at a distance of less than the size of light detecting element 124 (e.g., sensor pixel). The processor 310 can generate a sequence of sub-pixel shifted projection images of the specimen 400 based on light received by the plurality of light detecting elements 124. With a super-resolution algorithm, the processor 310 can obtain a high-resolution image of the specimen 400 based on the sequence of sub-pixel shifted projection images. The light guide structure introduces an inter-pixel separation through the guide layer, which can improve resolution even with a filter 170 in the light guides 114. For fluorescence/phosphorescence imaging, the specimen 400 may be illuminated by illumination 210 with excitation light from an illumination source 200 such as a laser or LED. The excitation light excites the fluorophores in the specimen 400. The excitation light is attenuated through the filter of the guide layer 110 so that only the fluorescence/phosphorescence signal can be detected. The processor 310 can generate a fluorescence/phosphorescence image of the specimen 400 based on the emissions received by the plurality of light detecting elements 124.

A. Bright-Field High-Resolution Imaging Schemes

High resolution bright field imaging can be accomplished with a light guided pixel device 100 having light guides 114 with filters 170 using a pixel super-resolution algorithm. An example of a suitable pixel super-resolution algorithm can be found in Sung Cheol, P., P. Min Kyu, and K. Moon Gi, "Super-resolution image reconstruction: a technical overview," Signal Processing Magazine, IEEE, 20(3), pp. 21-36 (2003), which is hereby incorporated by reference in its entirety for all purposes. Sub-pixel shifted images are captured by scanning the illumination source 200 to create different projections of the specimen 400 on the light detector layer 120. The portion of the guide layer 110 between the light guides 114 may help prevent light to cross over to adjacent light detecting elements 124, maintaining the resolution through filters 170 in the guide layer 110.

The scanning of the illumination source 200 may be accomplished using any variety of methods that may involve, for example, scanning stages or mirrors, LED arrays, a flat panel display screen, or other suitable devices. For example, the scanning illumination source 200 may be a device (e.g., smartphone) having a display (e.g., LCD) with a light element (e.g., set of one or more display pixels). The scanning illumination source 200 may be able to scan or otherwise translate the light element to a plurality of scanning positions at different scanning times. In one case, the scanning illumination source 200 may be able to scan or otherwise translate the light element to the various scanning positions at certain scanning times according to a scanning pattern. Illumination 210 from the light element at the different scanning locations generates shifted projections of the specimen 400 on the detector surface 126. During scanning, the plurality of light detecting elements 124 captures one or more sequences of sub-pixel shifted projection images. The processor 310 receives data for the sequence of light projections. The processor 310 can determine a motion vector of the sub-pixel shifted projections from the data for the sequence of sub-pixel shifted light projections. The processor 310 can construct one or more high resolution bright field images of the specimen 400 using a suitable super-resolution algorithm with the data from at least one of the sequences of sub-pixel shifted projection images of the specimen 400 and/or the determined motion vector.

The plurality of scanning locations may be in any suitable arrangement (e.g., array, circle, square, triangle, etc.). For example, the scanning locations may be in the form of an array (e.g., one-dimensional array, two-dimensional array, or combination of one-dimensional and two-dimensional arrays) of scanning locations. Each of the arrays may have any suitable dimensions (e.g., 2×1, 2×1, 100×200, 100×100, etc.). In one case, the scanning locations are be arranged in a two-dimensional (n×m) array of n×m scanning locations at: $(x_{i=1\ to\ n}, y_{j=1\ to\ m})$.

FIGS. 3(a), 3(b), and 3(c) are schematic drawings of components of a light guided pixel device 100 during an exemplary bright-field high-resolution imaging scheme, according to an embodiment of the invention. In FIGS. 3(a), 3(b), and 3(c), the light guided pixel device 100 includes a body 101 having a guide layer 110 having a plurality of light guides 112 and a light detector layer 120 having a plurality of light detecting elements 122. Each light guide 114 includes a filter 170. The guide layer 110 also has an outer surface 116 and an inner surface 118. The body 101 also includes a transparent layer 180 outside the outer surface 116 of the guide layer 110 of a suitable material having a suitable thickness. For example, the outer layer 180 may be made of a bio-compatible material for cells and other specimens 400 to be able to attach and grow well. In the illustrated example, a specimen 400 having two cells is located on the outer surface of the outer layer 180.

In the illustrated example, an illumination source 200 (not shown) provides illumination 210 from three scanning positions at scanning times $t=t_a$, $t_b$, and $t_c$ respectively in FIGS. 3(a), 3(b), and 3(c). The illumination 210 from the three scanning positions generates a sequence of three sub-pixel shifted projections of the specimen 400 on the outer surface 116 of the guide layer 110. A sequence of three sub-pixel shifted projections can refer to two or more sub-pixel shifted projection, where consecutively captured projections are located less than the size of a light detecting element (e.g., pixel size) from each other. The plurality of light detecting elements 124 can measure light of the sequence of sub-pixel shifted projections. Although three scanning positions are shown and three corresponding sub-pixel shifted projections are generated in the illustrated example, the imaging procedure may include any suitable number (e.g., 2, 3, 5, 10, 100, etc.) of scanning positions to generate the suitable number of sub-pixel shifted projections in other embodiments. The processor 310 can determine a motion vector of the sub-pixel shifted projections based on the light data from the sequence of sub-pixel shifted projection s. Using a suitable super resolution algorithm, the processor 310 can construct a high resolution image of the specimen 400 from the light data of the sequence of sub-pixel shifted projection images as captured by the plurality of light detecting elements 124.

B. Low Resolution Fluorescence Imaging Schemes

A fluorescent specimen can be imaged at low resolution using a light guided pixel device 100 by illuminating the entire specimen 400 at one time with illumination 210 of excitation light. The filter 170 in the light guides 114 blocks the excitation light from reaching the light detector layer 120 (e.g., photosensor), allowing the fluorescence signal to be detected by the light detecting elements 124 in the light detector layer 120. The filter material of the filter 170 may be selected according to the excitation and emission spectrum of the fluorescence dye and the excitation illumination source available. For the excitation, narrow-bandwidth light illumination sources such as laser or LEDs can be used. The resolution of the fluorescent images generated by this scheme can be based on the size (e.g., diameter) of a light detecting element (e.g., sensor pixel) in the plurality of light detecting elements 124.

Figure 4:
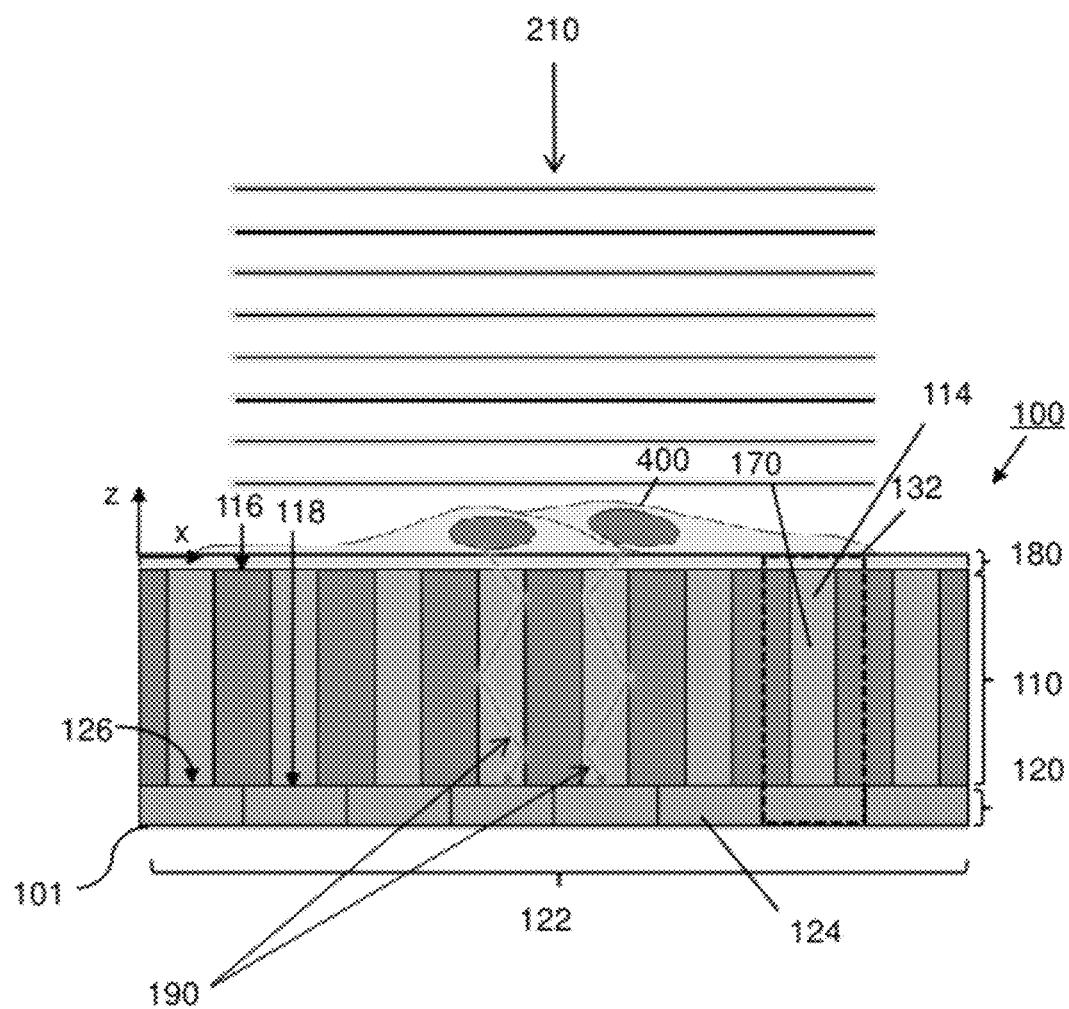
FIG. 4 is a schematic drawing of components of a light guided pixel device during an exemplary low resolution fluorescence imaging scheme, according to an embodiment of the invention.

FIG. 4 is a schematic drawing of components of a light guided pixel device 100 during an exemplary low resolution fluorescence imaging scheme, according to an embodiment of the invention. In FIG. 4, the light guided pixel device 100 includes a body 101 having a guide layer 110 having a plurality of light guides 112 and a light detector layer 120 having a plurality of light detecting elements 122. The guide layer 110 also has an outer surface 116 and an inner surface 118. The body 101 also includes a transparent layer 180 outside the outer surface 116 of the guide layer 110. The transparent layer 180 may be made of any suitable material of a suitable thickness. For example, the transparent layer 180 may be made of a bio-compatible material for cells and other specimens to be able to attach and grow well. Each light guide 114 includes a filter 170 for rejecting excitation light and passing emissions from activated fluorophores in a specimen 400 located outside the outer surface of the transparent layer 180. In the illustrated example, the specimen 400 includes two cells. The body 101 of the light guided pixel device 100 in FIG. 4 also includes eight discrete light guided pixels 132. Each light guided pixel 132 includes a guide layer 110 with a single light guide 114, a light detector layer 120 with a single light detecting element 124, and a portion of the transparent layer 180.

In FIG. 4, an illumination source 200 (not shown) provides illumination 210 with excitation light to the entire specimen 400. Any suitable illumination source 200 capable of providing illumination of a narrow-bandwidth of excitation light can be used such as a laser or LEDs. The excitation light activates fluorophores in the specimen 400. Emissions 190 from the fluorophores and excitation light are received by the light guides 114 in the guide layer 110. The light guides 114 channel light to the light detector layer 120. The filter 170 in the light guides 114 rejects the excitation light and passes the emissions 190. The plurality of light detecting elements 124 measures the emissions 190. The processor 310 receives a signal or signals with light data associated with the emissions 190 and constructs a low resolution fluorescence image of the specimen 400. The resolution of the specimen 400 is determined by the size of the light detecting elements 124 in the light detector layer 120.

C. High Resolution Fluorescence Imaging Schemes

To boost the resolution of the fluorescence imaging, a light guided pixel device 100 can use focus-spot array illumination in a high resolution fluorescence imaging scheme. An example of focus-spot array illumination can be found in Wu, J., et al., "*Wide field-of-view microscope based on holographic focus grid illumination,*" Opt. Lett., 35(13), pp. 2188-2190 (2010), which is hereby incorporated by reference in its entirety for all purposes. The array of light focus spots can generally only excite the fluorophores near the light focus spots. In some cases, the spacing between the light focus spots may be equal to or larger than the size of the light detecting element 132. In these cases, the fluorescence signal detected by each light detecting element 132 corresponds to the location of the illuminated spot on the specimen 400 associated with a single light focus spot.

The array of light focus spots can be scanned (e.g., raster scanned) to excite fluorophores in different parts of the specimen 400 on a time-varying basis. The light detecting elements 124 measure time varying light data (e.g., line scans) as the array of focus spots are scanned across the specimen 400. A processor 310 can compile the time varying light data including time varying emissions data to generate one or more fluorescence images with sub-pixel resolution. The resolution in this scheme may be based on the size of the focus spots.

In a high resolution fluorescence imaging scheme, the array of focus spots can be created by various methods including a microlens array, a Fresnel zone plate array and other diffractive optical elements, a holographic plate, and the talbot effect from an array of apertures. The illumination source 200 may include suitable structures and/devices for generating the array of focus spots. For example, the illumination source 200 may include a holographic element (e.g., holographic plate) or diffractive optical element (e.g., a Freznel zone plate (FZP), diffraction grating, photon sieve, etc.) and a beam generator (e.g., laser). The holographic element or diffractive optical element can transform a wavefront from the beam generator into the array of focus spots.

The array of focus spots may be a one-dimensional array, a two-dimensional array, or a combination of one and/or two dimensional arrays. Each focus spot may have a diameter of any suitable size. Some examples of suitable sizes include 0.4 microns, 0.6 microns, 0.8 microns, 1 micron, etc. Any suitable spacing (e.g., 5 microns, 10 microns, 15 microns, etc.) can be used between the focus spots.

Figure 5:
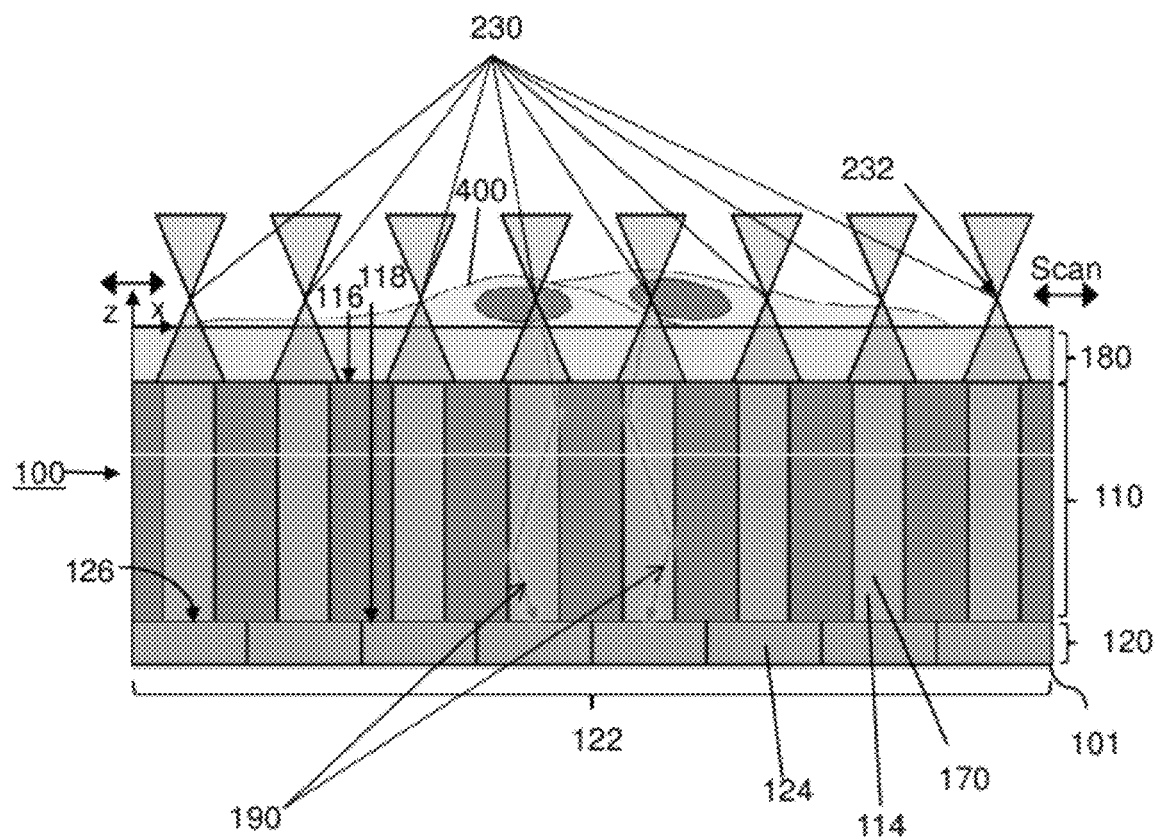
FIG. 5 is a schematic drawing of components of a light guided pixel device during an exemplary high resolution fluorescence imaging scheme, according to an embodiment of the invention.

FIG. 5 is a schematic drawing of components of a light guided pixel device 100 during an exemplary high resolution fluorescence imaging scheme, according to an embodiment of the invention. In FIG. 5, the light guided pixel device 100 includes a body 101 having a guide layer 110 having a plurality of light guides 112 and a light detector layer 120 having a plurality of light detecting elements 122. Each light guide 114 includes a filter 170. The guide layer 110 also has an outer surface 116 and an inner surface 118. The body 101 also includes a transparent layer 180 outside the outer surface 116 of the guide layer 110. The transparent layer 180 may be made of any suitable material of a suitable thickness. For example, the transparent layer 180 may be made of a bio-compatible material for cells and other specimens to be able to attach and grow well. In the illustrated example, a specimen 400 having two cells is located on the outer surface of the outer layer 180. The light guided pixel device 100 in FIG. 5 also includes an x-axis, a y-axis (not shown), and a z-axis. The x-axis and y-axis lie in a plane at the outer surface 116 of the guide layer 110. The z-axis is orthogonal to this plane.

In FIG. 5, an illumination source 200 (not shown) provides illumination 210 of excitation light in the form of an array of focus spots 230. The illumination 210 includes an array of converging spherical wavefront. The array of spherical wavefront forms the focal array of light spots 230. Each volume is hour-glass shaped, forming a focal cone converging to a focus spot 232 at a focal plane and spreading from the focal plane in a spreading volume. Fluorophores at the locations of the focus spots the specimen 400 are activated by the excitation light to generate emissions 190.

As the illumination source 200 scans the array of focus spots 230 across the specimen, fluorophores at different locations in the specimen are activated on a time-varying basis. The light detecting elements 124 in the light detecting layer 120 can receive light (e.g., emissions) and generate time varying light data (e.g., line scans) based on the light received as the array of focus spots 230 is scanned over the specimen 400. A processor 310 can combine the time varying light data to generate one or more fluorescence/phosphorescence of the specimen 400 or otherwise analyze the specimen 400.

III. On-Chip Applications

Microscopy is an essential tool in studying biological sciences. Recent advances in miniaturization of imaging systems can provide an inexpensive alternative for large microscopes in biology labs, allowing parallel imaging of large number of samples. Some examples of recent advances in miniaturizing imaging systems can be found in Cui, X., et al., "*Lensless high-resolution on-chip optofluidic microscopes for Caenorhabditis elegans and cell imaging,*" Proceedings of the National Academy of Sciences, 105(31), p. 10670 (2008), Seo, S., et al., "*Lensfree holographic imaging for on-chip cytometry and diagnostics. Lab on a Chip,*" 9(6), pp. 777-787 (2009), Breslauer, D., et al., Mobile phone based clinical microscopy for global health applications (2009), and Zheng, G., et al., "*Sub-pixel resolving optofluidic microscope for on-chip cell imaging. Lab on a Chip,*" 10(22), pp. 3125-3129 (2010), which are hereby incorporated by reference in their entirety for all purposes.

On-chip imaging systems with lower cost and smaller size can be used as an on-chip cell culturing platform, where one can image the cells throughout the time in a parallel manner. An example of automated imaging system can b found in Levin-Reisman, I., et al., "*Automated imaging with ScanLag reveals previously undetectable bacterial growth phenotypes*," Nat Meth, 7(9), pp. 737-739 (2010), where is hereby incorporated by reference in its entirety for all purposes. Combined with conventional incubator-based cell cultures, on-chip microscopes can help explore the time-resolved information in studying systems biology, cell growth and in-vitro drug screening where the counting and tracking individual cells in an in-situ and parallel manner is difficult with conventional methods such as bulky microscopes or plate readers.

A CMOS image sensor based on-chip imaging system has recently been developed using a pixel super-resolution algorithm and LCD screen illumination. An example of a super-resolution algorithm can be found in Sung Cheol, P., P. Min Kyu, and K. Moon Gi, "*Super-resolution image reconstruction: a technical overview*," Signal Processing Magazine, IEEE, 20(3), pp. 21-36 (2003). In this system, the specimen is placed on the sensor's surface and imaged in a sequence of pixelated low-resolution images with each frame obtained while raster scanning the bright pixels on the LCD screen as illumination. Then, these images are processed into a single high-resolution image using the pixel super-resolution algorithm. In this system, resolution comparable to those obtained by conventional 20×-40× objective microscopes can be achieved. The highest resolution may be achieved at the plane on the surface of the sensor.

The light guided pixel system 10 of embodiments may function as an on-chip lensless imaging system having one or more on-chip light guided pixel devices 100. Each on-chip light guided pixel device 100 can use a pixel super-resolution algorithm and include light guides 114 to provide a compact imaging platform for both bright-field and fluorescence high-resolution imaging of biological samples, rendering it a powerful tool in biological and medical studies.

In one on-chip light guided pixel system 10, one or more on-chip light guided pixel devices 100 may be used in an on-chip cell culture platform with imaging capabilities. The compact and low-cost nature of this system may allow a user to perform in-situ analysis of a culture, such as growth tracking, screening and cell counting.

Figure 6:
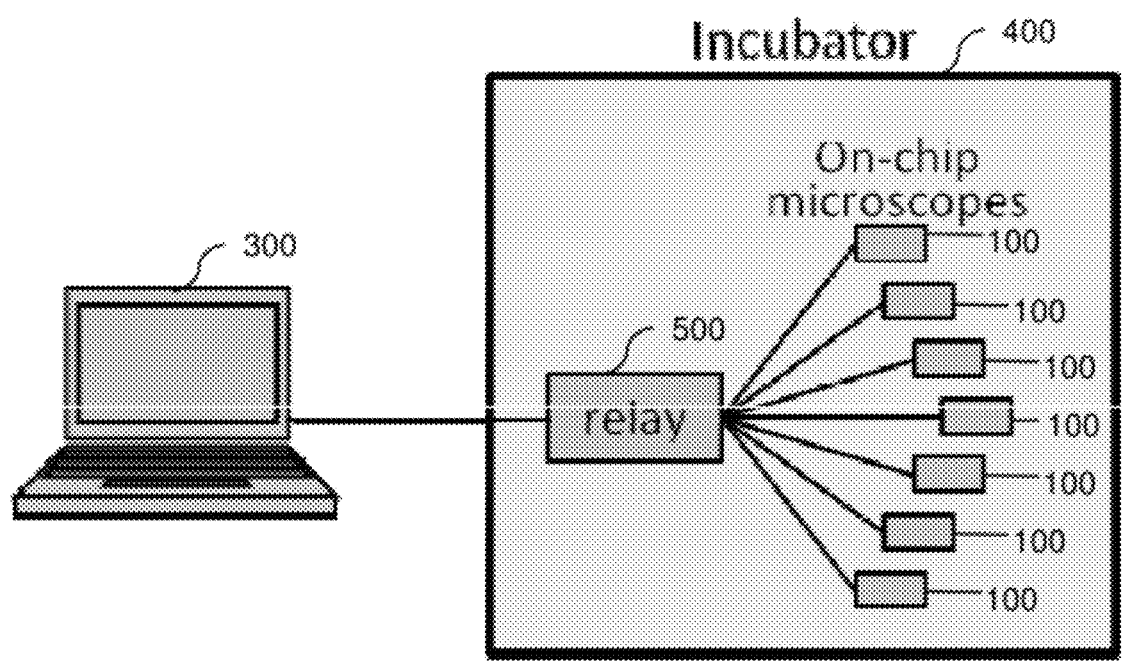
FIG. 6 is a schematic drawing of an on-chip light guided pixel system in an on-chip cell culture platform with parallel in-situ imaging for real-time analysis, according to an embodiment of the invention.

FIG. 6 is a schematic drawing of an on-chip light guided pixel system 10 in an on-chip cell culture platform with parallel in-situ imaging for real-time analysis, according to an embodiment of the invention. In FIG. 6, the on-chip light guided pixel system 10 includes a seven on-chip light guided pixel devices 100. The on-chip light guided pixel system 10 also includes a host computer 300, an incubator 400, and a relay 500. The on-chip light guided pixel devices 100 are in communication with the host computer 300 through the relay 500. The on-chip light guided pixel devices 100 are located within the incubator 400. Although seven light guided pixel devices 100 are shown, any suitable number (e.g., 1, 2, 4, 5, 6, 10, 100, etc.) may be included.

The light guided pixel system 10 also includes a host computer 300 having a processor 310, a computer readable medium (CRM) 320, and a display 330. The display 330 and the CRM 320 are in communication with the processor 310. The processor 310 is in communication with the light detector layer 120 of the light guided pixel device 100. Although a single light guided pixel device 100 is shown in FIG. 1, a light guided pixel system 10 of other embodiments may include multiple light guided pixel devices 100. The relay 500 (e.g., relay multiplexer) can relay information through signals from the multiple light guided pixel devices 100 to a processor 210 (not shown) in the host computer 300.

This on-chip multimodal imaging system can be made in a low-cost and compact manner with the ability to grow cells on them. The entire imaging system can be put in an incubator so that a user can image the cells in both bright-field and fluorescence. A simple chamber design can be put on the chip where cells and the culture medium can be stored. Multiple array of chambers or complex fluidic network can also be designed to provide control of chemical and mechanical environment. This system may be able to replace petridishes and well-plates in biology labs.

IV. Fabrication of Guide Layer with Light Guides

A light guided pixel device 100 can be fabricated using suitable conventional methods. The layers of a multilayer body 101 of embodiments of the light guided pixel device 100 can be made via additive and etching processes. Also, a guide layer 110 of an embodiment can be made separately and then aligned to the plurality of light detecting elements 122 of the light detector layer 120, or fabricated directly on the light detector layer 120. Suitable additive processes include electro- or electroless-plating on a predefined rod array. In one embodiment, a guide layer 110 with a plurality of light guides 112 in the form of apertures can be made by etching through a bulk material, such as thin metal sheet, silicon substrate or polymeric film.

The portion of the guide layer 110 between light guides 114 can be made of any suitable material that can block the light from crossing over to the adjacent light guide 114. For example, it can be any reflective metal, other material coated with thin reflective metal layer or low refractive index material in comparison to the light guide core as in fiber optic faceplates.

One method of fabricating the body 101 of the light guided pixel device 100 and other high aspect ratio metallic structures is by using a standard Lithographic, Galvano-formung, Abformung (LIGA) process. FIG. 7 is a schematic drawing of steps of a LIGA process that may be used to fabricate a body 101 of a light guided pixel device 100, according to an embodiment of the invention. In this process, a thin conductive seed layer 510 is deposited on the detector surface 126 of a light detector layer 120 (e.g., CMOS image sensor) or a silicon substrate, as shown in FIG. 7(*a*). In another step shown in FIG. 7(*b*), a tall rod array 520 may be made using a high aspect ratio photoresist, such as SU8. This tall rod array 520 can work as a mold for the electroplating step shown in FIG. 7(*c*). Once the metal 530 (e.g., Ni) is grown via electroplating or deposition, the photoresist can be removed as shown in FIG. 7(*d*). The remaining apertures 540 can be filled with the dye material (filter material) by spin coating or sonication to form the filter 170 to complete the guide layer 110. Once the light guides 114 are filled with the filter material forming the filters 170, a passivation layer 180 (not shown) may be placed on top of the guide layer 110 before conducting any biological imaging and analysis.

Another method of fabricating the body 101 of the light guided pixel device 100 is by using a reactive-ion etching (RIE) process or deep-RIE to process to fabricate a tall rod array 520 made of filter material (absorptive color filter, interference filter etc). In this method, a tall rod array 520 made of filter material (i.e. light guides 114 with filters 170) can be used as a mold for electroplating metal between the light guides 114 to form the guide layer 114. A reactive-ion etching (RIE) or deep-RIE process can be used to fabricate the tall rod array 520 with the filter material (absorptive color filter, interference filter etc). Depending on the dye type, the dye in the tall rod array 520 needs to be mixed with photoresist or other chemicals in order to maintain the shape during the electroplating process.

Figure 8:
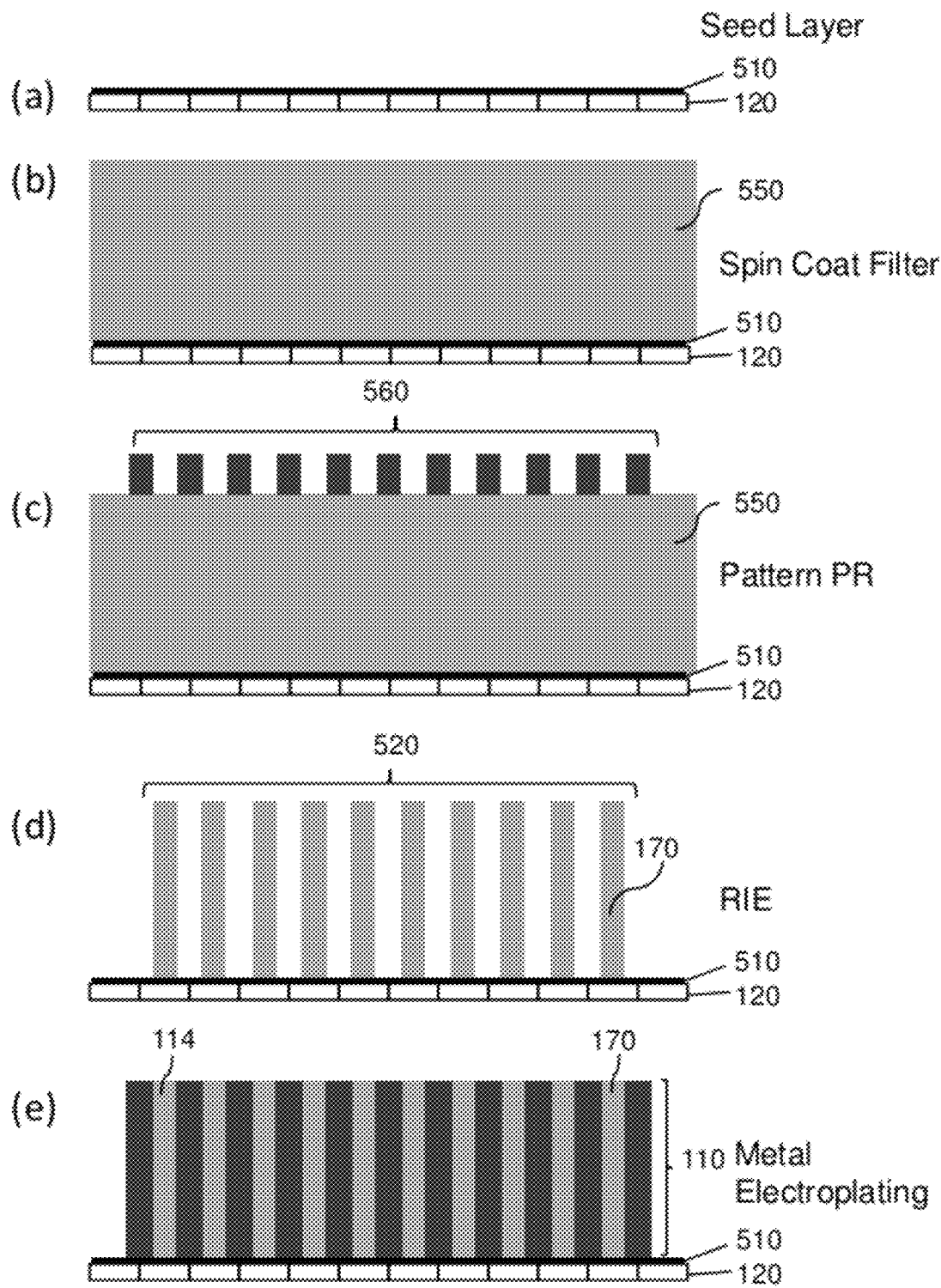
FIG. 8 is a schematic drawing of steps of a reactive-ion etching (RIE) process that may be used to fabricate a body of a light guided pixel device, according to an embodiment of the invention.

FIG. 8 is a schematic drawing of steps of a reactive-ion etching (RIE) process that may be used to fabricate a body 101 of a light guided pixel device 100, according to an embodiment of the invention. In this process, a thin conductive seed layer 510 is deposited on the detector surface 126 of a light detector layer 120 (e.g., CMOS image sensor) or a silicon substrate, as shown in FIG. 8(*a*). In FIG. 8(*b*), a spin coat filter layer 550 of filter material is deposited on the thin conductive seed layer. A pattern 560 made of photoresist material is added on the spin coat filter layer 550 in FIG. 8(*c*). In FIG. 8(*d*), a reactive-ion etching (RIE) or deep-RIE process is used to remove material leaving the tall rod array 520 of filters 170. The tall rod array 520 works as a mold for the electroplating step shown in FIG. 8(*e*). In some cases, a passivation layer 180 (not shown) may be placed on top of the guide layer 110 before conducting any biological imaging and analysis.

V. Computer Devices

Figure 9:
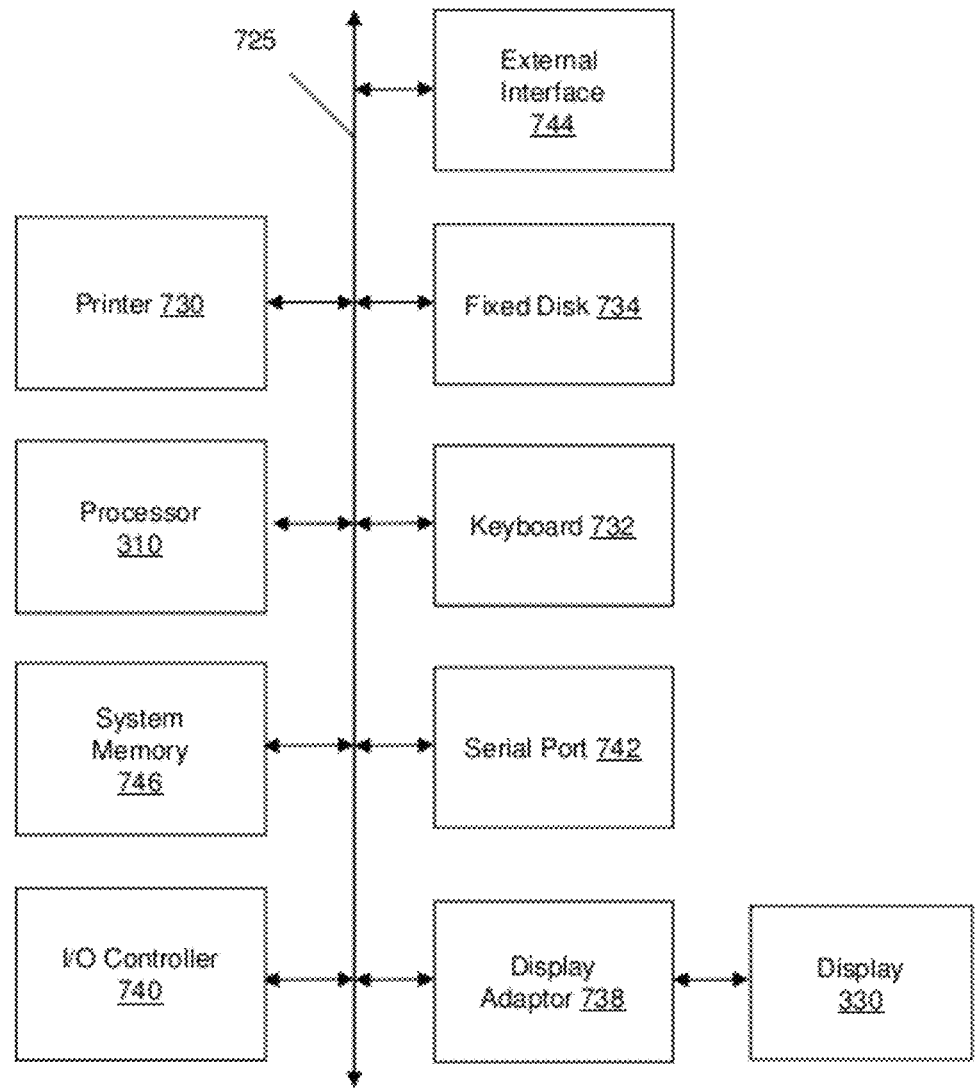
FIG. 9 is a block diagram of subsystems that may be present in computer devices that are used in the light guided pixel system, according to embodiments of the invention.

FIG. 9 shows a block diagram of subsystems that may be present in computer devices that are used in the light guided pixel system 10, according to embodiments of the invention. For example, the computer 200 in communication with the light guided pixel device 100 may have any suitable combination of components in FIG. 9.

The various components previously described in the Figures may operate using one or more computer devices to facilitate the functions described herein. Any of the elements in the Figures may use any suitable number of subsystems to facilitate the functions described herein. Examples of such subsystems or components are shown in a FIG. 9. The subsystems shown in FIG. 9 are interconnected via a system bus 725. Additional subsystems such as a printer 730, keyboard 732, fixed disk 734 (or other memory comprising computer readable media), display 330, which is coupled to display adapter 738, and others are shown. Peripherals and input/output (I/O) devices, which couple to I/O controller 740, can be connected to the computer system by any number of means known in the art, such as serial port 742. For example, serial port 742 or external interface 744 can be used to connect the computer apparatus to a wide area network such as the Internet, a mouse input device, or a scanner. The interconnection via system bus allows the central processor 310 to communicate with each subsystem and to control the execution of instructions from system memory 746 or the fixed disk 734, as well as the exchange of information between subsystems. The system memory 746 and/or the fixed disk 734 may embody a computer readable medium 320. Any of these elements may be present in the previously described features. A computer readable medium 320 according to an embodiment of the invention may comprise code for performing any of the functions described above.

In some embodiments, an output device such as the printer 730 or display 330 of the light guided pixel system 10 can output various forms of data. For example, the light guided pixel system 10 can output a fluorescence/phosphorescence image of a specimen 400 or other results of analysis.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

A recitation of "a", "an" or "the" is intended to mean "one or more" unless specifically indicated to the contrary.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

All patents, patent applications, publications, and descriptions mentioned above are hereby incorporated by reference in their entirety for all purposes. None is admitted to be prior art.

What is claimed is:

1. A light guided pixel configured for emissions detection, comprising:
    a guide layer comprising a light guide through an opaque or reflective material layer, the light guide comprising first and second opposing ends, wherein the first end is configured to receive incident light from outside the guide layer; and
    a light detector layer comprising a light detecting element proximal the second end of the light guide, the light detecting element configured to detect light emissions,
    wherein the detected light emissions received at the first end of the light guide from outside the guide layer are channeled to the second end and to the light detecting element, and
    wherein the light guide comprises a wavelength selective filter material for absorbing excitation light and passing light emissions based on wavelength selective properties of the wavelength selective filter material, wherein the absorbed excitation light and the passed light emissions are received from outside the first end of the light guide.

2. The light guided pixel configured for emissions detection of claim 1, wherein the light guide comprises
    a light transmissive region through the opaque or reflective material layer of the guide layer and
    a reflective wall,
    wherein the light transmissive region comprises the wavelength selective filter material.

3. The light guided pixel configured for emissions detection of claim 1, further comprising a transparent layer between the guide layer and the light detector layer.

4. A light guided pixel device configured for emissions imaging, comprising:
  a guide layer comprising a plurality of light guides through an opaque or reflective material, each light guide comprising first and second opposing ends, wherein each first end is configured to receive incident light from outside the guide layer, wherein the guide layer further comprises an inter-pixel separation of the opaque or reflective material between adjacent light guides of the plurality of light guides; and
  a light detector layer comprising a plurality of light detecting elements, each light detecting element configured to detect light emissions received from outside the guide layer at the first end of at least one light guide of the plurality of light guides,
  wherein the detected light emissions are channeled from each first end to each second end of the at least one light guide and to the light detecting element, and
  wherein one or more of the light guides comprises a wavelength selective filter material for absorbing excitation light and passing light emissions based on wavelength selective properties of the wavelength selective filter material, wherein the absorbed excitation light and the passed light emissions are received from outside the first end of each of the one or more light guides.

5. The light guided pixel device configured for emissions imaging of claim 4, wherein each of the light guides comprises
  a light transmissive region through the opaque or reflective material layer of the guide layer and
  a reflective wall,
  wherein the light transmissive region comprises the wavelength selective filter material.

6. The light guided pixel device configured for emissions imaging of claim 4, further comprising a transparent layer between the guide layer and the light detector layer.

7. The light guided pixel device configured for emissions imaging of claim 4, further comprising a processor configured to generate an emissions image of a specimen located between an illumination source and the guide layer, wherein the emissions image is associated with light emissions detected by the plurality of light detecting elements.

8. The light guided pixel device configured for emissions imaging of claim 4,
  wherein the light detector layer further comprises a processor configured to generate an emissions image of a specimen provided between an illumination source and the guide layer, and
  wherein the emissions image is associated with light emissions detected by the plurality of light detecting elements.

9. The light guided pixel device configured for emissions imaging of claim 4, wherein the plurality of light detecting elements are arranged in a two-dimensional array.

10. The light guided pixel device configured for emissions imaging of claim 4, further comprising a processor configured to generate a sequence of sub-pixel shifted projection images of a specimen located between a scanning illumination source and the guide layer, the sequence of sub-pixel shifted projection images corresponding to a plurality of scanning locations of the illumination source, the processor further configured to generate a sub-pixel resolution image of the specimen based on the sequence of sub-pixel shifted projection images.

11. The light guided pixel device configured for emissions imaging of claim 4,
  wherein the light detector layer further comprises a processor configured to generate a sequence of sub-pixel shifted projection images of a specimen located between a scanning illumination source and the guide layer, the sequence of sub-pixel shifted projection images corresponding to a plurality of scanning locations of the illumination source,
  wherein the processor is further configured to generate a sub-pixel resolution image of the specimen based on the sequence of sub-pixel shifted projection images.

12. A light guided pixel system configured for emissions imaging comprising:
  a light guided pixel device comprising
    a guide layer comprising a plurality of light guides through an opaque or reflective material, each light guide comprising first and second opposing ends, wherein each first end is configured to receive incident light from outside the guide layer, wherein the guide layer further comprises an inter-pixel separation of the opaque or reflective material between adjacent light guides of the plurality of light guides; and
    a light detector layer comprising a plurality of light detecting elements, each light detecting element configured to detect light emissions received from outside the guide layer at the first end of at least one light guide of the plurality of light guides, wherein the detected light emissions are channeled from each first end to each second end of the at least one light guide and to the light detecting element, wherein the light transmissive region comprises a wavelength selective filter material for absorbing excitation light and passing emissions based on wavelength selective properties of the wavelength selective filter material, wherein the absorbed excitation light and the passed light emissions are received from outside the first end of the light guide; and
  a processor in communication with the plurality of light detecting elements, the processor configured to generate one or more projection emissions images of a specimen located between an illumination source and the guide layer, the one or more projection emissions images based on data received from the plurality of light detecting elements and associated with the light emissions detected by the plurality of light detecting elements.

13. The light guided pixel system configured for emissions imaging of claim 12, wherein each light guide comprises
  a light transmissive region through the opaque or reflective material layer of the guide layer and
  a reflective wall,
  wherein the light transmissive region comprises the wavelength selective filter material.

14. The light guided pixel system configured for emissions imaging of claim 12, further comprising a transparent layer between the guide layer and the light detector layer.

15. The light guided pixel system configured for emissions imaging of claim 12,
  wherein the illumination source is configured to provide illumination from a plurality of scanning locations at different scanning times,
  wherein the one or more projection images is a sequence of sub-pixel shifted projection images corresponding to the plurality of scanning locations, and
  wherein the processor is further configured to generate a sub-pixel resolution image of the specimen based on the sequence of projection images.

16. A light guided pixel system configured for emissions imaging, the light guided pixel system comprising:
- a guide layer comprising a plurality of light guides through an opaque or reflective material, each light guide comprising first and second opposing ends, wherein each first end is configured to receive incident light from outside the guide layer, wherein the guide layer further comprises an inter-pixel separation of the opaque or reflective material between adjacent light guides of the plurality of light guides;
- a light detector layer comprising a plurality of light detecting elements;
- an array of light guided pixels, each light guided pixel comprising a light guide of the plurality of light guides and a corresponding light detecting element of the plurality of light detecting elements, the light detecting element configured to detect light emissions received from outside the guide layer at the first end of at least one light guide of the plurality of light guides, wherein the detected light emissions are channeled from each first end to each second end of the at least one light guide and to the light detecting element, wherein each light guide of the plurality of light guides further comprises a wavelength selective filter material for absorbing excitation light and passing light emissions based on wavelength selective properties of the wavelength selective filter material, wherein the absorbed excitation light and the passed light emissions are received from outside the first end of each light guide; and
- a processor configured to generate one or more projection emissions images of a specimen provided between an illumination source and the guide layer, the one or more emissions images associated with the light emissions detected by the plurality of light detecting elements.

17. The light guided pixel system configured for emissions imaging of claim 16,
- wherein the illumination source is configured to provide illumination from a plurality of scanning locations at different scanning times,
- wherein the one or more projection images is a sequence of sub-pixel shifted projection images corresponding to the plurality of scanning locations, and
- wherein the processor is further configured to generate a sub-pixel resolution image of the specimen based on the sequence of projection images.

18. The light guided pixel configured for emissions detection of claim 1, wherein the light guide is configured to channel the light emissions to a center area of the light detecting element.

19. The light guided pixel device configured for emissions imaging of claim 4, wherein each light guide is configured to channel the light emissions to a center area of the corresponding light detecting element of the plurality of light detecting elements.

20. The light guided pixel configured for emissions detection of claim 1, further comprising a multilayer body comprising the light guide layer disposed on the light detector layer.

21. The light guided pixel device configured for emissions imaging of claim 4, further comprising a multilayer body comprising the light guide layer disposed on the light detector layer.

* * * * *